US010905654B2

(12) United States Patent
Jia et al.

(10) Patent No.: US 10,905,654 B2
(45) Date of Patent: Feb. 2, 2021

(54) COMPOSITIONS OF BAKUCHIOL AND METHODS OF MAKING THE SAME

(71) Applicant: Unigen, Inc., Seattle, WA (US)

(72) Inventors: Qi Jia, Olympia, WA (US); Mei-Feng Hong, Seattle, WA (US)

(73) Assignee: Unigen, Inc., Tacoma, WA (US)

( * ) Notice: Subject to any disclaimer, the term of this patent is extended or adjusted under 35 U.S.C. 154(b) by 1102 days.

(21) Appl. No.: 14/807,712

(22) Filed: Jul. 23, 2015

(65) Prior Publication Data
US 2016/0022602 A1  Jan. 28, 2016

Related U.S. Application Data

(63) Continuation of application No. 13/049,731, filed on Mar. 16, 2011, now abandoned, which is a continuation of application No. 11/382,309, filed on May 9, 2006, now abandoned.

(60) Provisional application No. 60/679,337, filed on May 9, 2005.

(51) Int. Cl.
*A61K 31/05* (2006.01)
*A61K 36/487* (2006.01)
*A61K 9/00* (2006.01)

(52) U.S. Cl.
CPC .......... *A61K 31/05* (2013.01); *A61K 9/0014* (2013.01); *A61K 36/487* (2013.01); *Y02A 50/30* (2018.01)

(58) Field of Classification Search
None
See application file for complete search history.

(56) References Cited

U.S. PATENT DOCUMENTS

| 3,553,236 | A | 1/1971 | Hascher |
| 5,882,672 | A | 3/1999 | Kojima et al. |
| 6,054,584 | A | 4/2000 | Ma et al. |
| 6,348,204 | B1 | 2/2002 | Touzan |
| 6,350,476 | B1 | 2/2002 | Hou |
| 6,750,248 | B2 | 6/2004 | Yong et al. |
| 6,878,381 | B2 | 4/2005 | Collington |
| 7,714,026 | B2 | 5/2010 | Lin et al. |
| 9,713,596 | B2 * | 7/2017 | Hong .............. A61K 31/05 |
| 2004/0043089 | A1 | 3/2004 | Rabie |
| 2005/0048008 | A1 | 3/2005 | Gupta |
| 2005/0256209 | A1 | 11/2005 | Lin et al. |
| 2006/0251749 | A1 | 11/2006 | Jia et al. |
| 2008/0286217 | A1 | 11/2008 | Chaudhuri et al. |
| 2010/0189669 | A1 | 7/2010 | Hakozaki |
| 2011/0223267 | A1 | 9/2011 | Jia et al. |
| 2012/0201769 | A1 | 8/2012 | Hong et al. |

FOREIGN PATENT DOCUMENTS

| DE | 1900435 | | 7/1970 |
| DE | 3417234 A | * | 11/1985 |
| DE | 3417234 A1 | | 11/1985 |
| JP | 11-71231 A | | 3/1999 |
| JP | 2000-327581 A | | 11/2000 |
| JP | 2005-325120 A | | 11/2005 |
| KR | 10-2000-0007648 | | 2/2000 |
| WO | 2006/122160 A2 | | 11/2006 |
| WO | 2008/140673 A1 | | 11/2008 |

OTHER PUBLICATIONS

Chaudhuri et al., Bakuchiol in the management of acne-affected Skin, 2011, Cosmetics & Toiletries magazine, 126: 502-510.*
"Supplier's Corner: Bakutrol," Nutraceuticals World, Sep. 10, 2010, retrieved from http://nutraceuticalsworld.com/issues/2010-10/view_suppliers-corner/bakutrol/, on Oct. 7, 2015, 1 page.
Adhikari et al., "Antioxidant Activity of Bakuchiol: Experimental Evidences and Theoretical Treatments on the Possible Involvement of the Terpenoid Chain," *Chem. Res. Toxicol.* 16(9):1062-1069, 2003.
Agathiyar paripooranam 400, by Agasthiyar Pub: Rathina Nayakar & Sons, Thirumagal Vilakku Press, Chennai (1964) p. 65, F. ID: GD02/85.
Anuboga Vaithiya Navaneetham, by Abdulla Sahib Pub:Palani Thandayuthapani Devasthanam Publication, Directorate of Indian Systems of Medicine, Chennai. (1975) p. 518 , F. ID: KS01/121.
Arck et al., "Towards a "free radical theory of graying": melanocyte apoptosis in the aging human hair follicle is an indicator of oxidative stress induced tissue damage," The FASEB Journal, 20(9): E908-920, 1567-1569, 2006.
Arkaprakasah by Lankapatiravana—Edited and translation by Indradeva Tripathi; Krishnadas Academy, Varanasi, Edn. $1^{st}$ 1995 AD, p. 44 F. ID: AK14/54A.
Backhouse et al., "Active constitutes isolated from *Psoralea glandulosa* L. with anti-inflammatory and antipyretic activities," *J. Ethnopharmacol* 78(1):27-31, 2001.
Batap et al., "Preparation and in vitro evaluation of radioiodinated bakuchiol as an anti tumor agent," *Applied Radiation and Isotopes* 62(3):389-393, 2005.

(Continued)

Primary Examiner — Terry A McKelvey
Assistant Examiner — Catheryne Chen
(74) Attorney, Agent, or Firm — Sandra Poteat Thomspon; Finlayson Toffer Roosevelt & Lilly LLP

(57) ABSTRACT

The present invention provides compositions of bakuchiol (UP246) having low levels of impurities, particularly furanocoumarin impurities. The present invention further provides improved methods for the isolation, purification and analysis of compositions of bakuchiol. Finally, the present invention provides methods for using the purified bakuchiol compositions and formulations thereof for the prevention and treatment of various diseases and conditions mediated by cyclooxygenase (COX), lipoxygenase (LOX), minor inflammatory conditions and various microbial infections. The methods of this invention are comprised of administering to a host in need thereof an effective amount of the composition of this invention together with a pharmaceutically acceptable carrier.

20 Claims, 6 Drawing Sheets

(56) References Cited

OTHER PUBLICATIONS

Bayaaz-e-Kabir vol. II, Mohammad Azam Kahn, Daftar-al-Maseeh Karol Bagh, New Delhi, 1938, p. 108, F. ID: MA3/388.
Bhaisajya Ratnavali by Govinda Dasa—Edited by Rajeshvaradutta Shastri, Translated by Ambikaduttashastri: Chaukhamba Sanskrit Sansthan, Varanasi, Edn. $14^{th}$, 2001 [This book contains back references from 1000 B.C. to $18^{th}$ century], p. 271, F. ID: AK/1080.
Bharata Bhaisajya Ratnakara—Compiled by Naginadasa Chaganalala Saha, Translated by Gopinath Gupta—vol. III: B Jain Publishers, New Delhi, Edn. $2^{nd}$. Reprint, Aug. 1999. [This book contains back references from 1000 B.C. to $20^{th}$ century], p. 611 F. ID: RD/516.
Bharata Bhaisajya Ratnakara—Compiled by Naginadasa Chaganalala Saha, Translated by Gopinath Gupta—vol. II: B Jain Publishers, New Delhi, Edn. $2^{nd}$. Reprint, Aug. 1999. [This book contains back references from 1000 B.C. to $20^{th}$ century], p. 424 F. ID: P/1500.
Bharata Bhaisajya Ratnakara—Compiled by Naginadasa Chaganalala Saha, Translated by Gopinath Gupta—vol. IV: B Jain Publishers, New Delhi, Edn. $2^{nd}$. Reprint, Aug. 1999. [This book contains back references from 1000 B.C. to $20^{th}$ century], p. 621 F. ID: RS/1714.
Bharata Bhaisajya Ratnakara—Compiled by Naginadasa Chaganalala Saha, Translated by Gopinath Gupta—vol. III: B. Jain Publishers, New Delhi, Edn. $2^{nd}$. Reprint, Aug. 1999. [This book contains back references from 1000 B.C. to $20^{th}$ century], p. 562 F. ID: RD/360.
Billecke et al., "Human Serum Paraoxonase (PON1) Isozymes Q and R Hydrolyze Lactones and Cyclic Carbonate Esters," *Drug Metabolism and Disposition* 28(11):1335-1342, 2000.
Buckman et al., "COX-2 expression is induced by UVB exposure in skin: Implications for human the development of skin cancer," *Carcinogenesis* 19(5):723-729, 1998.
Chen et al., "Synthesis and structure-immunosuppressive activity relationships of bakuchiol and its derivatives," *Bioorganic & Medicinal Chemistry* 16:2403-2411, 2008.
Cho et al., "A Hepatoprotective Compound of *Psoralea corylifolia* on Tacrine-Induced Cytotoxicity in Hep G2 Cells," *Planta Med* 67(8):750-751, 2001.
Church et al., "Are cysteinyl leukotrienes involved in allergic responses in human skin?" *Clin. Exp. Allergy* 32:1013-1019, 2002.
Cuendet et al., "The Role of Cyclooxogenase and Lipoxygenase in Cancer Chemoprevention," *Drug Metabolism and Drug Interactions* 17(1-4):109-157, 2000.
Davis et al., "Postinflammatory Hyperpigmentation: A Review of the Epidemiology, Clinical Features, and Treatment Options in Skin of Color," *J. Clinical and Aesthetic Dermatology* 3(7): 20-31, 2010.
Dempke et al., "Cyclooxygenase-2: a novel target for cancer ehmotherapy?" *J. Can. Re.s Clin. Oncol.* 127:411-417, 2001.
Diawara et al., "A Novel Group of Ovarian Toxicants: The Psoralens," *J Biochem Molecular Toxicology* 13(3/4):195-203, 1999.
Diawara et al., "Psoralen-induced growth inhibition in Wistar rats," *Cancer Letters* 114:159-160, 1997.
Diawara et al., "Reproductive Toxicity of the Psoralens," *Pediatric Pathology and Molecular Medicine* 22:247-258, 2003.
English Translation of Japanese Office Action, dated Apr. 4, 2012, for corresponding Japanese Application No. JP 2008-511297, 2 Pages.
English Translation of Korean Office Action, dated Nov. 13, 2012, for corresponding Korean Application No. 10-2007-7028470, 5 pages.
Epstein, "Phototoxicity and Photoallergy," *Seminars in Cutaneous Medicine and Surgery* 18(4):274-284, 1999.
Erazo et al., "Antimicrobial Activity of *Psoralea Glandulosa* L.," *International Journal of Pharmacognosy* 35(5):385-387, 1997.
Fernandez-Obregon et al., "Current use of anti-infectives in dermatology," *Expert Rev. Anti Infect. Ther.* 3(4):557-591, 2005.
Ferrandiz et al., "Effect of Bakuchiol on Leukocyte Functions and Some Inflammatory Responses in Mice," *J. Pharm. Pharmacol.* 48(9):975-980, 1996.

Fischer et al., "Chemopreventative Activity of Celecoxib, a Specific Cyclooxygenase-2 Inhibitor, and Indomethacin Against Ultraviolet Light-Induced Skin Carcinogenesis," *Molecular Carcinogenesis* 25:231-240, 1999.
Fogh et al., "Modulation of Eicosanoid Formation by Lesional Skin of Psoriasis: an Ex vivo Skin Model," *Acta Derm Venereol* 73:191-193, 1993.
Goebel et al., "Procainamide, a Drug Cuasing Lupus, Induces Prostaglandin H Synthase-2 and Formulation of T Cell-Sensitizing Drug Metabolites in Mouse Macrophages," *Chem. Res. Toxicol.* 12:488-500, 1999.
Haraguchi et al., "Antioxidative Components of *Psoralea corylifolia* (Leguminosae)," *Phytother Res.* 16(6):539-544, 2002.
Haraguchi et al., "Inhibition of Mitochondrial Lipid Peroxidation by Bakuchiol a Meroterpene from *Psoralea corylifolia,*" *Planta Med* 66(6):569-571, 2000.
Hsu et al., "Bakuchiol, an antibacterial component of Psoralidium tenuiflorum," *Natural Product Research* 23(8):781-788, 2009.
Iwamura et al., "Cytoxicity of Corylifoliae Fructus, II. Cytoxicity of Bakuchiol and the Analogues," *Yakugaku Zasshi* 109(12):962-965, 1989.
Kaiyadevanighantau (Pathyapathyavibodhakah) by Kaiyadeva—Edited and translated by P.V. Sharma and Guru Prasad Sharma, Chaukhambha Orientalia, Varanasi, Edn. $1^{st}$, 1979, p. 130-131, F. ID: RS6/257A.
Kaiyadevanighantau (Pathyapathyavibodhakah) by Kaiyadeva—Edited and translated by P.V. Sharma and Guru Prasad Sharma, Chaukhambha Orientalia, Varanasi, Edn. $1^{st}$, 1979, p. 131, F. ID: RS/3125B.
Katsura et al., "In Vitro Antimicrobial Activities of Bakuchiol against Oral Microorganisms," *Antimicrob Agents Chemother* 45(11):3009-3013, 2001.
Khazaain-al-Advia, vol. I by Mohd Najmul Ghani Khan, Nadeem Yunus Printer/Sheikh Mohd Basheer & Sons, Lahore, 1911 AD, p. 680-681, F. ID: NA2/289.
Khazaain-al-Advia, vol. I by Mohd Najmul Ghani Khan, Nadeem Yunus Printer/Sheikh Mohd Basheer & Sons, Lahore, 1911 AD, p. 680, F. ID: NA2/289A.
Khazaain-al-Advia, vol. I by Mohd Najmul Ghani Khan, Nadeem Yunus Printer/Sheikh Mohd Basheer & Sons, Lahore, 1911 AD, p. 681, F. ID: NA2/289R.
Khazaain-al-Advia, vol. III by Mohd Najmul Ghani Khan, Nadeem Yunus Printer/Sheikh Mohd Basheer & Sons, Lahore, 1926 AD, p. 612, F. ID: JA6/589Z30.
Kim et al., "In vitro Protein Tyrosine Phosphatase 1B Inhibitory Phenols from the Seeds of *Psoralea corylifolia,*" *Planta Med* 71(1):87-99, 2005.
Korean Office Action dated Oct. 31, 2012, for corresponding Korean Application No. 10-2007-7028470, 4 pages.
Kowal-Bielecka, et al., "Evidence of 5-Lipoxygenase Overexpression in the Skin of Patients With Systemic Sclerosis," *Arthritis & Rheumatism* 44(8):1865-1875, 2001.
Krenisky et al., "Isolation and Antihyperglycemic Activity of Bakuchiol from *Otholobium pubescens* (Fabaceae), a Peruvian Medicinal Plant Used for the Treatment of Diabetes," *Biol. Pharm. Bull.* 22(10):1137-1140, 1999.
Lee et al., "Salicylic Acid Peels for the Treatment of Acne Vulgrais in Asian Patients," *Dermatol. Surg.* 29:1196-1199, 2003.
Leyden, "A review of the use of combination therapies for the treatment of acne vulgaris," *J. Am. Acad. Dermatol.* 49(3):200-210, 2003.
Mehta et al., "Metroterpenoids-I; *Psoralea Corylifolia* Linn.—1. Bakuchiol, A Novel Monoterpene Phenol," *Tetrahedron* 29(8):1119-1125, 1973.
Millikan, "The Rationale for Using a Topical Retinoid for Inflammatory Acne," *Am. J. Cln. Dermatol.* 4(2):75-80, 2003.
Moore et al., "COX-2 Inhibition, Apoptosis, and Chemoprevention by Nonsteroidal Anti-inflammatory Drugs," *Current Medicinal Chemistry* 7:1131-1144, 2000.
Muheet Azam, vol. I by Mohd Azam Khan, Matba Nizaami, Kanpur 1896 AD, p. 237, F. ID: MH3/278B.

(56) References Cited

OTHER PUBLICATIONS

Muller et al., "Modulation of Epidermal Tumor Development Caused by Targeted Overexpression of Epidermis-type 12S-Lipoxygenase," *Cancer Research* 62:4610-4616, 2002.

Murali et al., "An HPLC method for simultaneous estimation of psoralen, bakuchicin and bakuchiol in *Psoralea corylifolia*," *J. Natural Remedies* 2(1):76-80, 2002.

Murali et al., "Estimation of wedelolactone and demethylwedelolactone in Eclipta alba Hassk. by improved chromatographic analysis," *Journal of Natural Remedies* 2(1):99-101, 2002.

Newton et al., "The evaluation of forty-three plant species for in vitro antimycobatcerial activities; isolation of active constitutes from *Psoralea corylifolia* and *Sanguinaria Canadensis*," *J. Ethnopharmacol.* 79(1):57-67, 2002.

Nishijima et al., "The Bacteriology of Acne Vulgaris and Antimicrobial Susceptibility of *Propionibacterium acnes* and *Staphylococcus epidermidis* Isloated from Acne Lesions," *The Journal of Dermatology* 27:318-323, 2000.

Office Action, dated Jan. 13, 2013, for corresponding Japanese Patent Application No. 2008-511297, 2 pages.

Ohno et al., "Inhibitory Effects of Bakuchiol, Bavachin, an Isobavachalcone Isolated from Piper loungum on Melainin Production in B16 Mouse Melanoma Cells," *Biosci. Biotechnol. Biochem.* 74(7):1504-1506, 2010.

Pae et al., "Bakuchiol from *Psoralea corylifolia* inhibits the expression of inducible nitric oxide synthase gene via the inactivation of nuclear transcription factor-κB in RAW 264.7 macrophages," *International Immunopharmacol.* 1(9-10):1849-1855, 2001.

Patrono et al., "Functional Significance of Renal Prostacyclin and Thromboxane $A_2$ Production in Patients with Systemic Lupus Erythematosus," *The Journal of Clinical Investigation* 76:1011-1018, 1985.

Pentland et al., "Reduction of UV-induced skin tumors in hairless mice by selective COX-2 inhibition," *Carcinogenesis* 20(10):1939-1944, 1999.

Perry et al., "*Propionibacterium* acnes," *Letters in Applied Microbiology* 42:185-188, 2006.

Qiao et al., "Chemical fingerprint and quantitative analysis of Fructus Psoraleae by high-performance liquid chromatography," *J. Sep. Sci.* 30:813-818, 2007.

Quaraabaadeen Azam wa Akmal by Mohd Akmal Khan, Matba Siddiqi, Delhi/matba Mustafai, Delhi, 1909 AD, p. 351, F. ID: AH5/186C.

Rangari et al., "Chemisry & Pharmacology of Psoralea Corylifolia," *Indian Drugs* 29(15):662-670, 1992.

Rasaratnakarah by Nityanathasiddhah—Rasendra Khandam Comm. Datto Vallal Borakara, Ed. $2^{nd}$ 1986, Shri Gajanan Book Depot, (Pune). p. 849, F. ID: VK5/1388D.

Rasatantrasarah Evam Siddhaprayogasamgrahah;—part 1; Krishan Gopal Ayurevada Bhawan; Edn $8^{th}$; 1990 [This book contains back references from 1000 B.C. wo $20^{th}$ century], p. 100 F. ID, RS22/191.

Rasatantrasarah Evam Siddhaprayogasamgrahah;—part I; Krishan Gopal Ayurveda Bhawan; Edn $8^{th}$; 1990 [This book contains back references from 1000 B.C. to $20^{th}$ century], p. 518 F. ID: RS22/739.

Rasatantrasarah Evam Siddhaprayogasamgrahah;—part I; Krishan Gopal Ayurveda Bhawan; Edn $8^{th}$; 1990 [This book contains back references from 1000 B.C. to $20^{th}$ century], p. 529-530, F. ID: RS22/750.

Schneider et al., "Lipoxygenase Inhibitors From Natural Plant Sources. Part 1: Medicinal Plants with Inhibitory Activity on Arachidonate 5-lipoxygenase and 5-lipoxygenase/cyclooxygenase," *Phytotherapy Research* 19:81-102, 2005.

Scott et al., "Stem Cell factor Regulates the Melanocyte Cytoskeleton," *Pigment Cell Res.* 9:134-141, 1996.

Steele et al., "Mechanisms and applications of non-steroidal anti-inflammatory drugs in the chemoprevention of cancer," *Mutation Research* 523-524:137-144, 2003.

Sun et al., "DNA Polymerase and Topisomerase II Inhibitors from *Psoralea corylifolia*," *J. Nat. Prod.* 61(3):362-366, 1998.

Takizawa et al., "Gonadal Toxicity of an Ethanol Extract of *Psoralea Corylifolia* in Rat 90-day Repeated Dose Study," *The Journal of Toxicological Sciences* 27(2):97-105, 2002.

The Ayurvedic Pharmacopoeia of India—Part I, vol. I Edn. $1^{st}$, Reprinted—2001, Govt of India, Ministry of Health & Family Welfare, Deptt. of I.S.M. & H New Delhi. [This book contains back references from 1000 B.C. to $20^{th}$ century], p. 225, F. ID: RG/3515.

Third Party Submission filed in U.S. Appl. No. 13/365,172 on Dec. 21, 2012.

Third Party Written Observations filed in EP application serial No. 06759454.9 on Jul. 24, 2009.

Toombs, "Cosmetics in the Treatment of Acne Vulgaris," *Dematol. Clin.* 23:575-581, 2005.

Unigen, "Bakutrol™," Product information sheet, 2012, retrieved from http://www.unigen.net/products/bakutrol, on Oct. 7, 2015.

Vangasena by Vangasena—Commentator Shaligram Vaisya, Edited Shankar lalji Jain; Khemraj Shrikrishna Das Prakashan, Bombay, Edn. 1996 AD, p. 711, F. ID: AK11/2964.

Winer et al., "Expression of 12-lipoxygenase as a biomarker for melanoma carcinogenesis," *Melanoma Research* 12:429-434, 2002.

Brenner et al., "Modifying skin pigmentation—approaches through intrinsic biochemistry and exogenous agents," *Drug Dicov Today Dis Mech.* 5(2):e189-e199, 2008.

Ortonne et al., "Latest Insights into Skin Hyperpigmentation," *Journal of Investigative Dermatology Symposium Proceedings* 13:10-14, 2008.

Schwartz et al., "Postinflammatory Hyperpigmentation," Medscape.com, Jul. 27, 2009, 18 pages.

White et al., "Recent findings in the epidemiologic evidence, classification, and subtypes of acne vulgaris," *Journal of the American Academy of Dermatology* 39(2):S34-S37, 1998.

\* cited by examiner

Fig. 2A
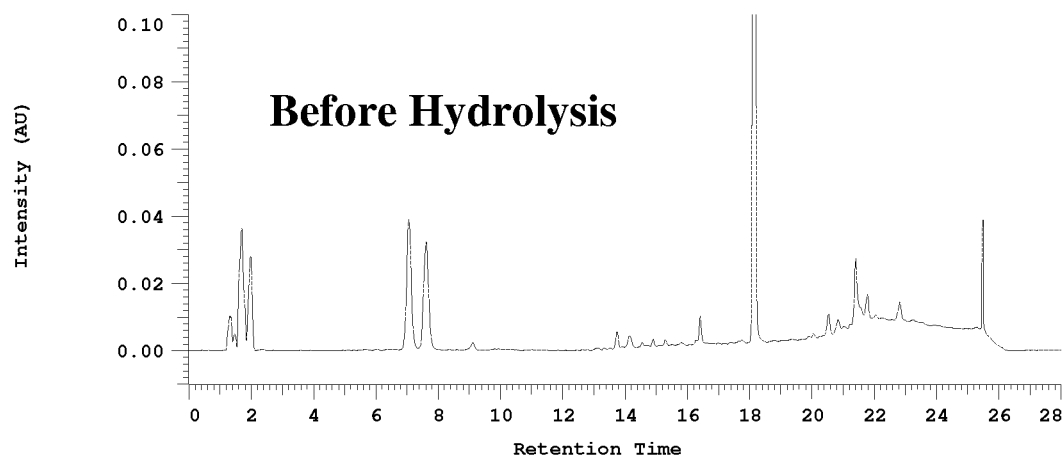
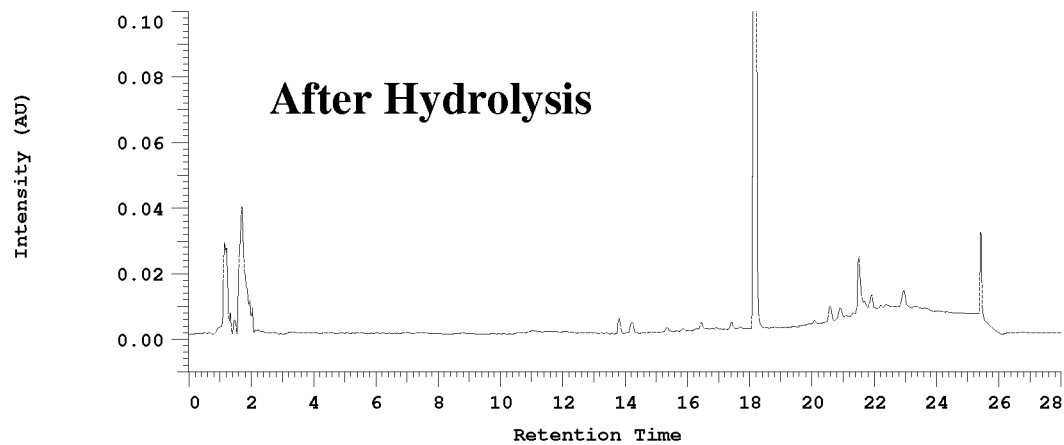
Fig. 2B

COMPOSITIONS OF BAKUCHIOL AND METHODS OF MAKING THE SAME

RELATED APPLICATIONS

This application is a continuation of U.S. application Ser. No. 13/049,731, files Mar. 16, 2011, which is a continuation of U.S. application Ser. No. 11/382,309, filed May 9, 2006, which claims the benefit of U.S. Provisional Application Ser. No. 60/679,337, filed May 9, 2005, entitled "Generation of High Purity Bakuchiol as a Therapeutic Agent," which is incorporated herein by reference in its entirety.

FIELD OF THE INVENTION

The present invention relates to compositions of bakuchiol and compounds related thereto having low levels of impurities, particularly furanocoumarin impurities. The present invention provides improved methods for the isolation, purification and analysis of compositions of bakuchiol. Finally, the present invention provides methods for using the purified bakuchiol compositions and formulations thereof for the prevention and treatment of various diseases and conditions mediated by cyclooxygenase (COX), lipoxygenase (LOX), minor inflammatory conditions and various microbial infections.

BACKGROUND OF THE INVENTION

Bakuchiol, the structure of which is illustrated below, is a phenolic compound having a single hydroxyl group on the aromatic ring and an unsaturated hydrocarbon chain. It has been isolated from the seeds of *Psoralea. corylifolia* L. (Luguminosae) and the aerial part of *Psoralea. glandulosa* L. (Papilionaceae).

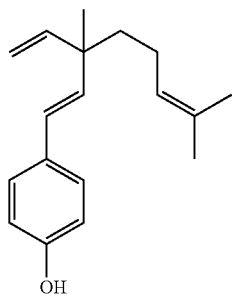

Bakuchiol

Bakuchiol, extracted from the plant *Psoralea corylifolia*, has been shown to have anti-tumor, anti-oxidant (Haraguchi et al. (September 2002) Phytother Res. 16(6):539-544), cytotoxic ((December 1989) Yakugaku Zasshi. 109(12):962-965), anti-microbial (Newton et al. (January 2002) J Ethnopharmacol. 79(1):57-67) and hepatoprotective activity (Cho et al. (November 2001) Planta Med. 67(8):750-751). It has also been shown to be a topoisomerase II inhibitor (Sun et al. (March 1998) J Nat Prod. 61(3):362-366). Bakuchiol inhibits PTPIB activity in a dose-dependent manner, displaying $IC_{50}$ values of 20.8+/−1.9 μM (Kim et al. (January 2005) Planta Med. 71(1):87-99). The preparation and in vitro evaluation of radioiodinated bakuchiol as an anti tumor agent has been reported by Batap et al. ((March 2005) Appl Radiat Isot. 62(3):389-393). The terpenoid chain of bakuchiol has been reported to be critical to its anti-oxidant activity (Adhikari et al. (September 2003) Chem Res Toxicol. 16(9):1062-1069).

Bakuchiol has also been reported as being a useful compound for the development of antibacterial agents against oral pathogens and as having great potential for use in food additives and mouthwash for preventing and treating dental caries (Katsura et al. (November 2001) Antimicrob Agents Chemother. 45(11):3009-3013). The anti-inflammatory and antipyretic activity guided fractionation of the active extracts of *Psoralea corylifolia* resulted in the isolation of bakuchiol together with three other active compounds: cyclobakuchiols A and B and angelicin. (Backhouse et al. (November 2001) J Ethnopharmacol. 78(1):27-31). Bakuchiol reportedly controls leukocytic functions such as eicosanoid production, migration and degranulation in the inflammatory site and is a weak inhibitor of secretary and intracellular PLA2. It dose-dependently reduces the formation of LTB4 and TXB2 by human neutrophils and platelet microsomes, respectively (Ferrandiez et al. (September 1996) J Pharm Pharmacol. 48(9):975-980). It also inhibits the expression of the inducible nitric oxide synthase gene via the inactivation of nuclear transcription factor-kappaB in RAW 264.7 macrophages. (Pae et al. (September 2001) International Immunopharmacol. 1(9-10): 1849-1855). Inhibition of mitochondrial lipid peroxidation by bakuchiol has also been reported (Haraguchi et al. (August 2000) Planta Med. 66(6):569-571). The isolation and antihyperglycemic activity of bakuchiol isolated from *Otholobium pubescens* (Fabaceae) is described by Krenisky et al. in Biol Pharm Bull. (October 1999) 22(10):1137-1140). Finally, a crude extract referred to as Buguzhi agent, containing bakuchiol, as well as, a number of other coumarin type compounds has been reported as promoting bone healing (US2004/0043089A1).

Bakuchiol, therefore, is a biologically active natural product having a great deal of potential for use in the prevention and treatment of various diseases and conditions. However, there are currently a number of limitations associated with the use of this compound due primarily to its low concentration in natural sources, as well as the presence of co-existing toxic components. One of the main problems related to the use of bakuchiol compositions isolated from plants in the *Psoralea* genus is the presence of psoralens, such as psoralen and isopsoralen, the structures of which are set forth below. Psoralens, also known as furanocoumarins, are naturally occurring secondary metabolites in plants, including many fruits and vegetables.

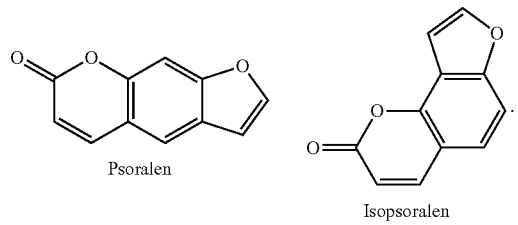 [SMILES: O=c1ccc2cc3ccoc3cc2o1 ; O=c1ccc2ccc3occc3c2o1]

Psoralen

Isopsoralen

A number of health risks have been associated with the handling, topical application and ingestion of psoralen-containing plants and synthetic psoralens. Psoralens are well known to be phototoxic agents, which increase the sensitivity of skin to ultra violet radiation and promote skin cancer (Epstein (1999) Med. Surg. 18(4):274-284). Psoralen has been shown to induce growth inhibition in rats (Diawara et al. (1997) Cancer Lett. 114(1-2):159-160). Gonadal toxicity from crude extracts of Psoralea plants has been linked directly with the disruption of the hypothalamus-pituitary-gonadal axis (Takizawa et al. (2002) J. Toxicological Sciences 27(2):97-105). Oral administration of the psoralens, bergapten (5-methoxypsoralen) and xanthotoxin (8-methoxypsoralen) in the diet of female rats reduced birthrates, the number of implantation sites, pups, corpora lutea, full and empty uterine weight, and circulating estrogen levels in a dose-dependent manner (Diawara et al. (1999) J. Biochem. Molecular Toxicology 13(3/4): 195-203). Psoralens have also been shown to induce the mRNAs of the liver enzymes CYP1A1 and UGT1A6, suggesting that enhanced metabolism of estrogens by psoralens may explain the reproductive toxicity and the observed reduction of ovarian follicular function and ovulation (Diawara et al. (May-June 2003) Pediatr Pathol Mol Med. 22(3):247-58.) Psoralen and isopsoralen account for about 0.1-2% of the dry weight of Psoralea seeds and about 1-20% of the weight in ethanol and other organic solvent crude extracts. There remains a need for a method for removing toxic compounds, such as psoralen and isopsoralen, as well as other coumarins in order to enhance the purity and safety of bakuchiol compositions, particularly those isolated from plant sources.

The release and metabolism of arachidonic acid (AA) from the cell membrane results in the generation of pro-inflammatory metabolites by several different pathways. Arguably, two of the most important pathways to inflammation are mediated by the enzymes lipoxygenase (LOX) and cyclooxygenase (COX). These are parallel pathways that result in the generation of leukotrienes and prostaglandins, respectively, which play important roles in the initiation and progression of the inflammatory response. These vasoactive compounds are chemotaxins, which promote infiltration of inflammatory cells into tissues and serve to prolong the inflammatory response.

Inhibition of the COX enzyme is the mechanism of action attributed to most non-steroidal anti-inflammatory drugs (NSAIDS). There are two distinct isoforms of the COX enzyme (COX-1 and COX-2), which share approximately 60% sequence homology, but differ in expression profiles and function. COX-1 is a constitutive form of the enzyme, which has been linked to the production of physiologically important prostaglandins, which help to regulate normal physiological functions, such as platelet aggregation, protection of cell function in the stomach and maintenance of normal kidney function. (Dannhardt and Kiefer (2001) Eur. J. Med. Chem. 36:109-26). The second isoform, COX-2, is a form of the enzyme that is inducible by pro-inflammatory cytokines, such as interleukin-1β (IL-1β) and other growth factors. (Herschmann (1994) Cancer Metastasis Rev. 134: 241-56; Xie et al. (1992) Drugs Dev. Res. 25:249-65). This isoform catalyzes the production of prostaglandin $E_2$ (PGE2) from arachidonic acid (AA).

Inhibitors that demonstrate dual specificity for COX and LOX would have the obvious benefit of inhibiting multiple pathways of arachidonic acid metabolism. Such inhibitors would block the inflammatory effects of prostaglandins (PG), as well as, those of multiple leukotrienes (LT) by limiting their production. This includes the vasodilation, vasopermeability and chemotactic effects of PGE2, LTB4, LTD4 and LTE4, also known as the slow reacting substance of anaphalaxis. Of these, LTB4 has the most potent chemotactic and chemokinetic effects. (Moore (1985) in Prostanoids: pharmacological, physiological and clinical relevance, Cambridge University Press, N.Y., pp. 229-230).

Because the mechanism of action of COX inhibitors overlaps that of most conventional NSAID's, COX inhibitors are used to treat many of the same symptoms, including pain and swelling associated with inflammation in transient skin conditions and chronic diseases in which inflammation plays a critical role. Consequently, the enzymes responsible for generating these mediators of inflammation have become the targets in the development of a number of novel drugs aimed at the treatment of inflammation, which contributes to the pathogenesis of diseases such as rheumatoid arthritis, osteoarthritis and Alzheimer's disease.

Transient skin conditions include treatment of inflammation associated with minor abrasions or contact dermatitis, as well as, skin conditions that are directly associated with the prostaglandin and leukotriene pathways, such as skin hyperpigmentation, age spots, vitilago, systemic lupus erythromatosus, psoriasis, carcinoma, melanoma, and other mammalian skin cancers. The use of COX inhibitors has been expanded to include diseases, such as systemic lupus erythromatosus (SLE) (Goebel et al. (1999) Chem. Res. Toxicol. 12:488-500; Patrono et al. (1985) J. Clin. Invest. 76:1011-1018), as well as rheumatic skin conditions, such as scleroderma. COX inhibitors are also used for the relief of inflammatory skin conditions that are not of rheumatic origin, such as psoriasis, in which reducing the inflammation resulting from the overproduction of prostaglandins could provide a direct benefit. (Fogh et al. (1993) Acta Derm Venerologica 73:191-193). Recently over expression of 5-lipoxygenase in the skin of patients with system sclerosis has been reported. This has led to the suggestion that the LOX pathway may be of significance in the pathogenesis of system sclerosis and may represent a valid therapeutic target. (Kowal-Bielecka (2001) Arthritis Rheum. 44(8: 1865). Finally, the increased enzymatic activity of both the COX-2 and 5-LOX at the site of allergen injections suggests the potential for using dual COX/LOX inhibitors to treat the symptoms of both the early and late phases of the skin allergic response. (Church (2002) Clin. Exp. Allergy. 322 (7):1013).

Prostaglandins and leukotrienes also play important roles in the physiological and pathological processes of wounds, burns, scald, acne, microbial infections, dermatitis, and many other diseases and conditions of the skin. The activation of a pro-inflammatory cascade after thermal or chemical burns with significantly elevated cyclooxygenase and lipoxygenase activities are well documented and play an important role in the development of subsequent severe symptoms and immune dysfunction that may lead to multiple organ failure. (Schwacha (2003) Burns 29(1):1; He (2001) J. Burn Care Rehabil. 22(1):58).

In addition to their use as anti-inflammatory agents, another potential role for COX inhibitors is in the treatment of cancer. Over expression of COX has been demonstrated in various human malignancies and inhibitors of COX have been shown to be efficacious in the treatment of animals with skin tumors. While the mechanism of action is not completely understood, the over expression of COX has been shown to inhibit apoptosis and increase the invasiveness of tumorgenic cell types. (Dempke et al. (2001) J. Can. Res. Clin. Oncol. 127:411-17; Moore and Simmons (2000) Current Med. Chem. 7:1131-1144). Up regulated COX production has been implicated in the generation of actinic keratosis and squamous cell carcinoma in skin. Increased amounts of COX were also found in lesions produced by DNA damage. (Buckman et al. (1998) Carcinogenesis 19:723). Therefore, control of expression or protein function of COX would seem to lead to a decrease in the inflammatory response and the eventual progression to cancer. In fact. COX inhibitors such as indomethacin and Celebrex™ have been found to be effective in treating UV induced erythema and tumor formation. (Fischer (1999) Mol. Carcinog. 25:231; Pentland (1999) Carcinogenesis 20:1939). Recently, the over expression of lipoxygenase has also been shown to be related to epidermal tumor development (Muller (2002) Cancer Res. 62(16):4610) and melanoma carcinogenesis (Winer (2002) Melanoma Res. 12(5):429). The arachidonic acid (AA) metabolites generated from lipoxygenase pathways play important roles in tumor growth related signal transduction suggesting that that the inhibition of lipoxygenase pathways should be a valid target to prevent cancer progression. (Cuendet (2000) Drug Metabol Drug Interact 17(4):109; Steele (2003) Mutat Res. 523-524:137). Thus, the use of therapeutic agents having dual COX/LOX inhibitory activity offers significant advantages in the chemoprevention of cancer.

Acne is a chronic disease of the pilosebaceous unit characterized by excess production of sebum by the sebaceous glands, follicular epithelial desquamation, bacterial proliferation and inflammation. Hormone imbalance, microbial infection and inflammation are three of the major factors associated with the onset of acne (Toombs (2005) Dermatol. Clin. 23(3):575-581; Nishijima et al. (2000) J. Dermatol. 27(5):318-323). Current therapeutic agents for the prevention and treatment of acne include anti-inflammatory agents, such as retinoids, antimicrobial agents and hormonal drugs. (Leyden (2003) J. Am. Acad. Dermatol. 49(3 Suppl):S200).

The principal bacterial species associated with acne are *Propionibacterium acnes* and gram-positive *Staphylococcus epidermidis* (Perry and Lambert (2006) Lett. Appl. Microbiol. 42(3):185-188). Current therapeutic agents include benzoyl peroxide and other antimicrobial drugs, such as Ampicillin and Gentamicin (Fermandez et al. (2005) Expert Rev. Anti Infect Ther. 3(4):557-591). Unfortunately, drug resistance by both *Propionibacterium acnes* and *Staphylococcus epidermidis* has been reported (Nishijima et al. (2000) J. Dermatol. 27(5):318-323).

The topical application of anti-inflammatory drugs, such as retinoids (Millikan (2003) J. Am. Acad. Dermatol. 4(2): 75) and the COX inhibitor salicylic acid (Lee (2003) Dermatol Surg 29(12):1196) have also been clinically demonstrated to be an effective and safe therapy for the treatment of acne. Additionally, the use of nonsteroidal anti-inflammatory drugs (NSAIDs) are well documented as therapeutic agents for common and uncommon dermatoses, including acne, psoriasis, sun burn, erythema nodosum, cryoglobulinemia, Sweet's syndrome, systemic mastocytosis, urticarial, liverdoid and nodular vasculitis. (Friedman (2002) J. Cutan Med. Surg. 6(5):449).

Periodontal disease is an inflammation and infection of some or all of the tooth support structures (gingiva, cementum, periodontal ligament, alveolar bone and other tissues surrounding the teeth). Gingivitis (gums) and periodontitis (gums and bone) are the two main forms of periodontal disease. According to National Oral Information distributed by the National Institute of Dental and Craniofacial Research, an estimated 80 percent of American adults currently have some form of periodontal disease. Periodontal disease is initiated when a pellicle forms on a clean tooth or teeth. This pellicle attracts aerobic gram-positive bacteria (mostly actinomyces and streptococci), which adhere to the tooth forming plaque. Within days the plaque thickens, the underlying bacteria run out of oxygen and anaerobic motile rods and spirochetes begin to populate the subgingival area. Endotoxins released by the anaerobic bacteria cause inflammation, gum tissue destruction and even bone loss. There are four primary stages of periodontal disease that can be characterized as indicated below. The destructive impact of periodontal disease goes beyond dental hygiene and health, in that microscopic lesions resulting from periodontal disease have been found in the liver, kidneys, and brain of some affected persons.

| Four Stages of Periodontal Disease | |
|---|---|
| Grade 1 | Inflammation |
| Grade 2 | Inflammation, edema, gingival bleeding upon probing |
| Grade 3 | Inflammation, edema, gingival bleeding upon probing, pustular discharge—slight to moderate bone loss |
| Grade 4 | Inflammation, edema, gingival bleeding upon probing, pustular discharge, mobility—severe bone loss |

Current methods for treating periodontal disease are limited with control of the infection being the primary goal. (Genco et al. (1990) in *Contemporary Periodontics*, The C.V. Mosby Company, St. Louis, pp. 361-370). Common anti-microbial or anti-plaque agents include chlorhexidine, Triclosan, stannous fluoride, Listerine, hydrogen peroxide, cetylpyridimiun chloride and sanguinarine alkaloids. Prescription anti-microbial mouth rinse, antiseptic chip, antibiotic gel/micro-spheres, and enzyme suppressant-doxycycline are the preferred non-mechanical/physical options to treat and control periodontal disease. Unfortunately, there is currently no single periodontal medication which functions to both control the inflammation as well as inhibit the infection.

It is to be understood that both the foregoing general description and the following detailed description are exemplary and explanatory only and are not restrictive of the invention as claimed.

SUMMARY OF THE INVENTION

The present invention includes a novel composition of matter comprised of bakuchiol, which is substantially free of impurities, particularly furanocoumarin impurities. This composition of matter is also referred to herein as UP256. In some embodiments, the composition is obtained from the family of plants including, but not limited to Luguminosae, Papilionaceae, Lauraceae and Magnoliaceae. In other embodiments, the composition is obtained from a plant or plants selected from the genus of plants including, but not limited to *Psorlea, Sassafras, Magnolia* and *Astractylodes*. In preferred embodiments, the plant is selected from the group including, but not limited to *Psoralea corylifolia* L. (Luguminosae) or *Psoralea glandulosa* L. (Papilionaceae). The composition of the invention may be obtained from the whole plant or from one or more individual parts of the plant including, but not limited to the seeds, stems, bark, twigs, tubers, roots, root bark, young shoots, rhixomes, flowers and other reproductive organs, leaves and other aerial parts.

The amount of bakuchiol in the composition can be in the range of about 14 to 100 weight percent (%) depending on the method of extraction and the extent of purification of the crude extract. In one embodiment the amount of bakuchiol in the composition is in the range of 30% to 100%. In other embodiments the amount of bakuchiol in the composition is selected from the group consisting of at least 30%, at least 35%, at least 40%, at least 45%, at least 50%, at least 60%, at least 70%, at least 80%, or at least 90%. In a preferred embodiment, the amount of bakuchiol in the composition is approximately 30%.

An impurity includes any substance that is unwanted in the bakuchiol composition. Typically, the impurities present in the bakuchiol compositions are a result of the process employed to produce them, including both isolation from natural sources and synthetic methods. For example, in the isolation of bakuchiol from natural sources impurities include furanocoumarins, such as psoralen, isopsoralen and other coumarin type components.

The present invention also includes improved methods for isolating and purifying crude compositions of bakuchiol and related compounds obtained from natural sources. The improved method for isolating and purifying these compositions includes the steps of extraction of the compounds from a plant source, hydrolysis of the crude extract with a basic solution, and purification by a method including but not limited to column chromatography, extraction followed by crystallization, solvent partition, recrystallization and combinations thereof. Crude extracts purified in this manner are essentially free of furanocoumarin impurities such as psoralen and isopsoralen. Thus, the potential phototoxicity, topical irritation, carcenogenecity, and reproductive toxicity associated with these compounds are essentially eliminated. The purity of these compositions following isolation and purification by the methods of the instant invention is in a range selected from about 27% to 100%.

Also included in the present invention is a method for analyzing compositions of bakuchiol, which enables detection and quantification of impurities. In this embodiment of the invention, the method for analyzing compositions of bakuchiol is comprised of the step of analyzing said compositions by high-pressure liquid chromatography (HPLC). Analysis by HPLC enables quantification of the various components in the mixture and also provides a means to track bakuchiol, psoralen, isopsoralen and other natural components in *Psoralea* plants to guide the extraction, hydrolysis and purification processes.

The present invention also includes methods for the prevention and treatment of COX and LOX mediated diseases and conditions of the skin, mouth, teeth and gums. The method for preventing and treating COX and LOX mediated diseases and conditions of the skin, mouth, teeth and gums is comprised of administering, preferably topically, to a host in need thereof an effective amount of a composition comprising bakuchiol, which is substantially free of furanocumarin impurities together with a pharmaceutically acceptable carrier. As noted above, the amount of bakuchiol in the composition is in the range of 27% to 100%. In preferred embodiments the amount of bakuchiol in the composition is approximately 30%. Also as noted above, in preferred embodiments, the bakuchiol is isolated from a plant or plants in the *Psorlea* genus of plants.

COX and LOX mediated diseases or conditions of the skin include, but are not limited to, acne, dandruff, sun burn, thermal burns, topical wounds, minor inflammatory conditions caused by fungal, microbial and viral infections, vitilago, systemic lupus erythromatosus, psoriasis, carcinoma, melanoma, as well as other mammal skin cancers, skin damage resulting from exposure to ultraviolet (UV) radiation, chemicals, heat, wind and dry environments, wrinkles, saggy skin, lines and dark circles around the eyes, dermatitis and other allergy related conditions of the skin. COX/LOX mediated diseases and conditions of the mouth, teeth and gums, include, but not limited to periodontal diseases, oral pre-cancerous conditions, oral cancers, and other oral malignancies, sensitive gums and teeth, sequelae, pulpitis, irritation, pain and inflammation caused by the physical implantation of oral dentures, trauma, injuries, bruxism and other minor wounds in mouth, on the gums or on the tongue, dental plague and calculus, tooth decalcification, proteolysis and caries (decay).

The present invention further includes methods for the prevention and treatment of other COX and LOX mediated diseases and conditions, including but not limited to general joint pain and stiffness, lack of mobility and loss of physical function due to pathological conditions of osteoarthritis and rheumatoid arthritis, menstrual cramps, arteriosclerosis, obesity, diabetes, Alzheimer's disease, respiratory allergic reaction, chronic venous insufficiency, psoriasis, chronic tension headache, migraine headaches, inflammatory bowl disease, prostate cancer and other solid tumors.

The method for preventing and treating said COX and LOX mediated diseases and conditions is comprised of administering to a host in need thereof an effective amount of a composition comprising bakuchiol, which is substantially free of furanocumarin impurities together with a pharmaceutically acceptable carrier. As noted above, the amount of bakuchiol in the composition is in the range of 27% to 100%. In preferred embodiments the amount of bakuchiol in the composition is approximately 30%. Also as noted above, in preferred embodiments, the bakuchiol is isolated from a plant or plants in the *Psorlea* genus of plants.

Further included in the present invention are methods for the prevention and treatment of diseases and conditions of the skin, mouth, teeth or gums mediated by microbial infections, including but not limited to bacterial, viral and fungal infections, said method comprising administering to a host in need thereof an effective amount of a pharmaceutical composition comprised of bakuchiol, which is substantially free of furanocoumarin impurities together with a pharmaceutically acceptable carrier. Diseases and conditions of the skin, mouth, gums and teeth mediated by microbial infections include, but are not limited to dandruff, acne, athletes foot, periodontal diseases, selected from the group consisting of caries, gingivitis, periodontitis, pulpitis, periodontal conditions caused by the physical implantation of oral dentures, trauma, injuries, bruxism, neoplastic and other degenerative processes; material alba, pellicles, dental plagues, calculus and stains.

In one embodiment, the bacterium is selected from *Propionibacterium acnes* or *Staphylococcus epidermidis*.

The compositions of this invention can be administered by any method known to one of ordinary skill in the art. The modes of administration include, but are not limited to, enteral (oral) administration, parenteral (intravenous, subcutaneous, and intramuscular) administration and topical application. In preferred embodiments the compositions are administered topically. The method of prevention and treatment according to this invention comprises administering internally or topically to a patient in need thereof a therapeutically effective amount a composition comprised of bakuchiol, which is substantially free of impurities, particularly furanocoumarin impurities.

It is to be understood that both the foregoing general description and the following detailed description are exemplary and explanatory only and are not restrictive of the invention as claimed.

BRIEF DESCRIPTION OF THE DRAWINGS

FIG. 2A illustrates the HPLC chromatograms of *Psoralea* extracts before hydroxide hydrolysis reaction.

FIG. 2B illustrates the HPLC chromatograms of *Psoralea* extracts after sodium hydroxide hydrolysis reaction.

DETAILED DESCRIPTION OF THE PREFERRED EMBODIMENT

Figure 1:
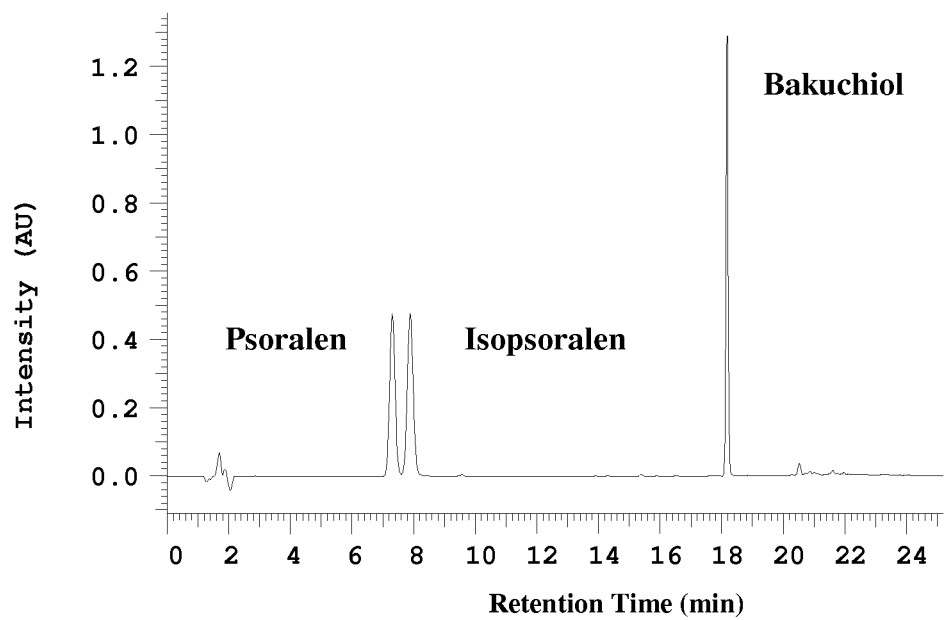
FIG. 1 illustrates the HPLC chromatogram of a representative extract from *Psoralea* plants. Two furanocoumarins—psoralen and isopsoralen are present in an equal amount in the extract.

The present invention includes compositions of bakuchiol (UP246) having low levels of impurities. Included in the present invention are improved methods for the isolation and purification of compositions of bakuchiol. Also included in the present invention is a method for analyzing compositions of bakuchiol, which enables the detection and quantification of various impurities. Further included in this invention is a method for using the purified bakuchiol compositions and formulations thereof for the prevention and treatment of various diseases and conditions mediated by cyclooxygenase (COX), lipoxygenase (LOX), minor inflammatory conditions and various microbial infections.

Various terms are used herein to refer to aspects of the present invention. To aid in the clarification of the description of the components of this invention, the following definitions are provided.

It is to be noted that the term "a" or "an" entity refers to one or more of that entity. As such, the terms "a" or "an", "one or more" and "at least one" are used interchangeably herein.

"Bakuchiol" as used herein refers to the compound having the following formula:

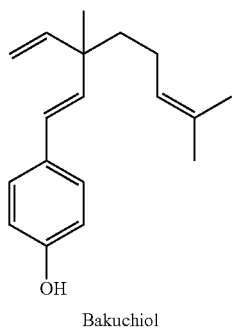 [SMILES: C=CC(C)(/C=C/c1ccc(O)cc1)CCC=C(C)C]

Bakuchiol wherein the central double-bond may be either cis or trans. Phenolic compounds structurally related to bakuchiol are also included within this definition.

As used herein the term "impurity" includes any substance that is not wanted in the bakuchiol composition, typically resulting from the isolation of bakuchiol from natural sources. The term impurity includes, but is not limited to furanocoumarin compounds selected from the group including but not limited to psoralen, isopsoralen and other coumarin type impurities. Impurities also refer to impurities resulting from synthetic processes to obtain these compositions.

"Therapeutic" as used herein, includes treatment and/or prophylaxis. When used, therapeutic refers to humans as well as other animals.

"Pharmaceutically or therapeutically effective dose or amount" refers to a dosage level sufficient to induce a desired biological result. That result may be the alleviation of the signs, symptoms or causes of a disease or any other alteration of a biological system that is desired.

"Placebo" refers to the substitution of the pharmaceutically or therapeutically effective dose or amount dose sufficient to induce a desired biological that may alleviate the signs, symptoms or causes of a disease with a non-active substance.

A "host" or "patient" is a living subject, human or animal, into which the compositions described herein are administered. Thus, the invention described herein may be used for veterinary as well as human applications and the terms "patient" or "host" should not be construed in a limiting manner. In the case of veterinary applications, the dosage ranges can be determined as described below, taking into account the body weight of the animal.

Note that throughout this application various citations are provided. Each citation is specifically incorporated herein by reference in its entirety.

The present invention includes a novel composition of matter comprised of bakuchiol, which is substantially free of impurities, particularly furanocoumarin impurities. This composition of matter is also referred to herein as UP256. In some embodiments, the composition is obtained from a plant or plants selected from the *Psorlea* genus of plants. In preferred embodiments the plant is selected from the group including, but not limited to *Psoralea corylifolia* L. (Luguminosae) or *Psoralea glandulosa* L. (Papilionaceae). The composition of the invention may be obtained from the whole plant or from one or more individual parts of the plant including, but not limited to the seeds, stems, bark, twigs, tubers, roots, root bark, young shoots, rhixomes, flowers and other reproductive organs, leaves and other aerial parts.

The amount of bakuchiol in the composition can be in the range of about 14 to 100 weight percent (%) depending on the method of extraction and the extent of purification of the crude extract. In one embodiment the amount of bakuchiol in the composition is in the range of 30% to 100%. In other embodiments the amount of bakuchiol in the composition is selected from the group consisting of at least 30%, at least 35%, at least 40%, at least 45%, at least 50%, at least 60%, at least 70%, at least 80%, or at least 90%. In a preferred embodiment, the amount of bakuchiol in the composition is approximately 30%.

An impurity includes any substance that is unwanted in the bakuchiol composition. Typically, the impurities present in the bakuchiol compositions are a result of the process employed to produce them, including both isolation from natural sources and synthetic methods. For example, in the isolation of bakuchiol from natural sources impurities include furanocoumarins, such as psoralen, isopsoralen and other coumarin type components.

The present invention also includes improved methods for isolating, analyzing and purifying crude compositions of bakuchiol obtained from natural sources. The improved method for isolating and purifying these compositions includes the steps of extraction of the compound from a plant source, hydrolysis of the crude extract with a basic solution, and purification by a method including but not limited to column chromatography, extraction followed by crystallization, solvent partition, recrystallization and combinations thereof. Crude extracts purified in this manner are essentially free of furanocoumarin impurities such as psoralen and isopsoralen.

A method for analyzing compositions of bakuchiol using high pressure liquid chromatography (HPLC) is described in Example 1 (Table 1). Analysis by HPLC enables quantification of the various components in the mixture and also provides a means to track bakuchiol, psoralen, isopsoralen and other natural components in *Psoralea* plants to guide the extraction, hydrolysis and purification processes.

The efficiency of bakuchiol extraction from plant sources was evaluated using six different organic solvent systems under two sets of extraction conditions as described in Example 2. The results are set forth in Table 2. With reference to Table 2, it can be seen that bakuchiol can be extracted from *Psoralea* plants with any number of organic solvents and/or combinations thereof. The amount of bakuchiol in the various extracts ranged from a maximum of 29.1% to 13.7% by weight. It was determined that extraction with petroleum ether provided the highest purity bakuchiol in the crude extract with good recovery. A representative HPLC chromatogram of a crude extract is illustrated in FIG. 1. With reference to this figure it can be seen that the crude extract contained bakuchiol as well as the furanocoumarin impurities psoralen and isopsoralen. Example 3 describes a large scale extraction with petroleum ether at 70° C.

The efficacy of purification of crude bakuchiol extracts by column chromatography is demonstrated in Example 4. Eight different types of resins were evaluated specifically for their ability to separate bakuchiol from furanocoumarin impurities. Both silica gel and CG-161 resins demonstrated satisfactory separation. Column chromatographic separation of crude plant extracts on an industrial scale, however, is typically not economically feasible in that it requires expensive equipment and reagents and experienced personnel, not to mention the extremely low loading capacity of these samples due to the complexity of crude plant extracts.

Examples 5-7 describe a novel, economical method for separating bakuchiol from furanocoumarin impurities, said method comprising treatment of compositions containing said impurities with a base. As illustrated by the following scheme, using NaOH for purposes of illustration, treatment with base opens up the lactone ring of the furanocoumarins, thereby converting them into the corresponding salts of carboxylic acids, which can then be easily separated from the remainder of the mixture by a variety of methods.

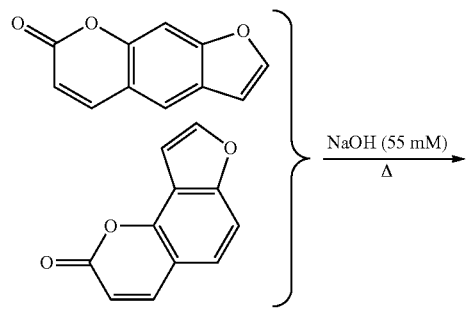
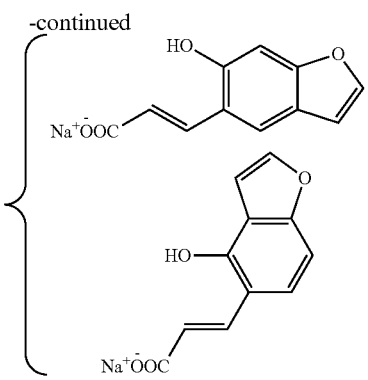

The basic solution can be selected from any base which can be used to open lactone rings, including, but not limited to sodium hydroxide, potassium hydroxide, calcium hydroxide and lithium hydroxide. The solution can be selected to have different concentration and pH values to maximize the conversion to the acid salt. The reaction mixture can also be heated under different temperature and pressures to maximize the reaction rate, efficiency and yield.

The course of the reaction can be followed by HPLC to ensure complete conversion of the coumarins into their respective carboxylic acid salts. The HPLC chromatograms of the crude composition before and after hydrolysis are illustrated in FIGS. 2A and B. Upon completion of the reaction (as determined by HPLC), the reaction solution can be processed using various methods, including but are not limited to column chromatography extraction followed by crystallization, solvent partition, recrystallization or combinations thereof. Crude extracts purified in this manner are essentially free of furanocoumarin impurities such as psoralen and isopsoralen.

With reference to Examples 5-7, upon hydrolysis under a variety of conditions followed by solvent partition, the furanocoumarins, psoralen and isopsoralen, are effectively removed from the bakuchiol composition. Additionally, the purity of bakuchiol is enhanced from about 10-30% to 30%-50%. Organic solvents that can be used for solvent partition include, but are not limited to petroleum ether, ethyl acetate, ethyl ether, hexane, chloroform, propanol, butanol, and methylene chloride, as well as other water immiscible organic solvents.

In one embodiment, which is described in Example 7, the crude reaction mixture is loaded directly onto a column followed by elution with a polar solvent. According to this embodiment compositions comprised of 70% to 100% of bakuchiol can be obtained. In Example 7, following hydrolysis the crude reaction mixture was loaded directly onto a CG-161 cd column followed by elution with methanol to provide highly pure (approximately 99%) bakuchiol. Other types of resins that can be used according to this embodiment include, but are not limited to XAD (Amerlite). CG-71/CG-161 or other type of polystyrene resins; ion exchange resins and silica gel. The column can be eluted with solvents selected from the group including, but not limited to water, methanol/water, ethanol/water, acetone/water and acetonitrile/water as well as other combinations of polar solvents. It is worth noting that the loading capacity of the column after hydrolysis was much higher than prior to hydrolysis. Additionally, the color of these highly pure furanocoumarin free, bakuchiol compositions was light brown and they were very stable with respect to both color and composition of the active agent, making them particularly suitable for formulation, storage and cosmetic applications.

In alternate embodiments, the crude reaction mixture can first be extracted with an organic solvent followed by further purification by chromatography and/or solvent partition and/or recrystallization. As noted above, depending on the method of extraction and extent of further purification bakuchiol compositions comprised of between about 30% and 100% are readily obtainable.

The present invention includes methods for using the purified bakuchiol compositions and formulations thereof for the prevention and treatment of various diseases and conditions mediated by cyclooxygenase (COX), lipoxygenase (LOX), minor inflammatory conditions and various microbial infections. The biological properties and safety of these unique furanocoumarin free bakuchiol compositions, referred to herein as UP256, were evaluated as described in Examples 8-11.

In Example 8, a highly pure composition of UP256 (MH-258-12-08, 99% purity) was tested for inhibition of both the COX-1 and COX-2 enzymes. UP256 showed potent inhibitory activity for both enzymes. The $IC_{50}$ for COX-1 was determined to be 2.34 µM, while $IC_{50}$ for COX-2 was quantified at 78 µM. Thus, this composition provides a more balanced modulation of the COX-1 and COX-2 enzymes than conventional COX inhibitors. For example, aspirin, a COX-1 selective inhibitor, which is more than 150 times more effective against COX-1 versus COX-2, causes gastrointestinal side effects. Conversely. Vioxx®, Celebrex® and Bextra®, which are selective COX-2 inhibitors having 50-200 times more potency against COX-2, do not cause as much gastrointestinal damage, however, these COX-2 selective drugs increase cardiovascular risks. The novel composition of matter disclosed herein on the other hand provide the best modulation of the eicosanoid pathway without the stomach irritation caused by COX-1 selective NSAIDs and cardiovascular risks posed by COX-2 selective inhibitors.

It is also significant that the mechanism of action for COX inhibition by UP256 is completely different than that of NSAIDs. Aspirin, Vioxx®, Celebrex® and Bextra® irreversibly bind to the COX enzyme through covalent bonds to form tightly bound enzyme-inhibitor complexes. This interaction completely changes the active site of the enzyme and the side pocket and destroys the enzyme. (Walker and Kurumbal et al. (2001) Biochem. 357:709-718). UP256, on the other hand, inhibits the COX enzyme through a weaker and reversible binding. In this interactive process, the structure and function of the COX enzyme are not irreversibly altered which results in a much better tolerance and safety profile.

Figure 6:
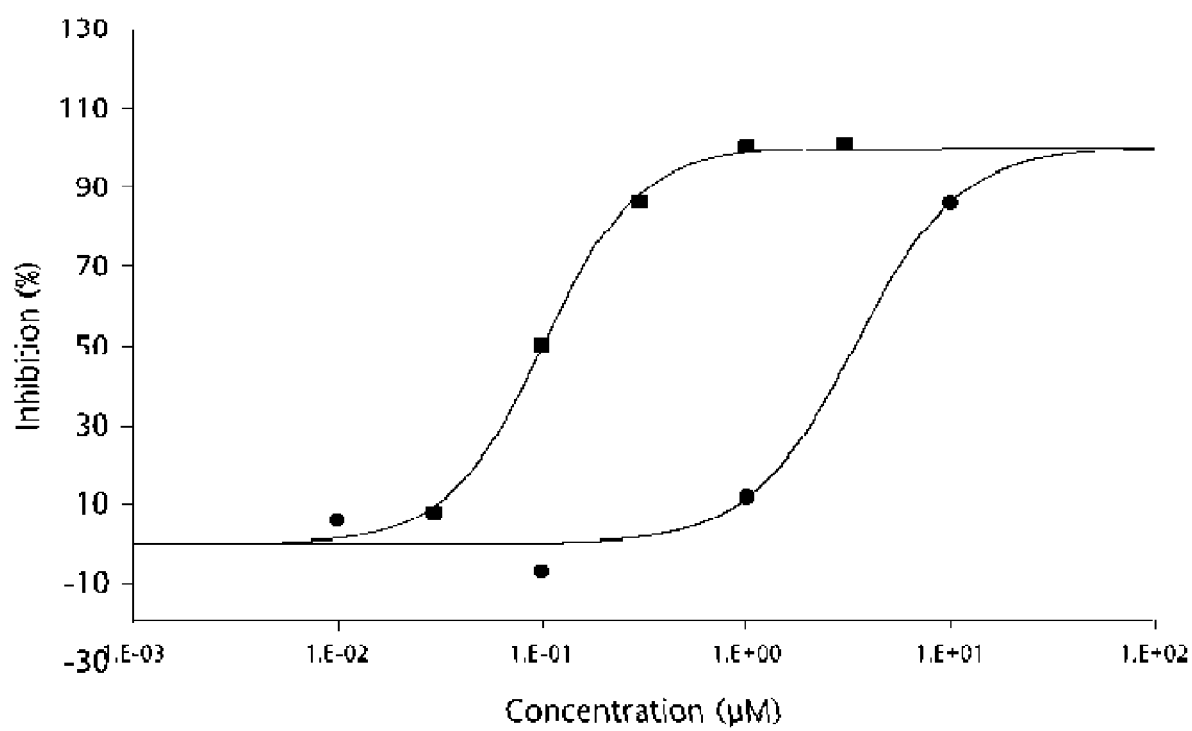
FIG. 6 depicts graphically a dose response curve of the inhibition of the activity of the enzyme 5-lipoxygenase (5-LO) by a UP256 composition (#MH-258-12-08 -●-) relative to positive control—NDGA (-■-).

Example 9 describes a LOX inhibition assay. The inhibition of LOX results in a decrease in the accumulation of phagocytic leukotrienes, which are directly associated with the symptoms of chronic inflammation, and also reduces potential gastrointestinal side effects. Such efficacy is demonstrated in Example 9. With reference to Example 9, the highly pure UP256 composition. MH-258-12-08 (99% purity) was tested in duplicate at four concentrations against the human 5-lipoxygenase (5-LO or 5-LOX) enzyme. The COX-2 inhibitory activity was confirmed by measurement of dose response and $IC_{50}$ (the concentration required to inhibit 50% of the enzyme's activity). The dose response curve is depicted in FIG. 6. The $IC_{50}$ for LOX inhibition was determined to be 3.41 µM. Thus, UP256 provides the additional benefit of significantly reducing leukotriene production. This reduction in leukotriene production is by far superior to traditional non-steroidal anti-inflammatory drugs such as ibuprofen.

Example 10 describes an experiment designed to determine the anti-microbial activity UP256. With reference to Example 10, UP256 was tested in duplicate at eight concentrations for the inhibition of six different microbes. It was found that UP256 inhibited two specific microbes, *Propionibacterium acnes* and gram-positive *Staphylococcus epidermidis*, at a minimum effective concentration of 1 µg/mL. Both of these microbes are directly associated with acne, dermatitis, and other skin infections. UP256 also showed moderate inhibition of *Trichophyton mentagrophytes* at a concentration 30 µg/mL. No inhibition was observed for *Epidermophyton floccosum, Microsporum canis* or *Pityrosporum ovale*.

UP256, at concentrations of 30% and 70%, was tested for acute toxicity in mice as described in Example 10. The mice tested were given an oral daily of 2 g/kg for 14 days. Mice showed no adverse effects in terms of weight gain and blood chemistry. Additionally, no toxicity was observed in any of the major organs tested. In conclusion, weight, blood work and histological data, was no different for the treatment group than for the control group. No adverse effects were observed in the fourteen-day study. Thus, it can be concluded that UP256 has a solid safety profile.

Finally, UP256 has a partition coefficient of log P=6.13. The partition coefficient of a chemical compound provides a thermodynamic measure of its hydrophilicity/lipophilicity balance and thus its potential bioavailability. Having a partition coefficient of 6.13 means this compound has high cell membrane penetration and bioavailability when formulated in a delivery system.

The present invention therefore includes methods for the prevention and treatment of COX and LOX mediated diseases and conditions of the skin, mouth, teeth and gums. The method for preventing and treating COX and LOX mediated diseases and conditions of the skin, mouth, teeth and gums is comprised of administering, preferably topically, to a host in need thereof an effective amount of a composition comprising bakuchiol, which is substantially free of furanocumarin impurities together with a pharmaceutically acceptable carrier. As noted above, the amount of bakuchiol in the composition is in the range of 27% to 100%. In preferred embodiments the amount of bakuchiol in the composition is approximately 30%. Also as noted above, in preferred embodiments, the bakuchiol is isolated from a plant or plants in the *Psorlea* genus of plants.

COX and LOX mediated diseases or conditions of the skin include, but are not limited to, acne, dandruff, sun burn, thermal burns, topical wounds, minor inflammatory conditions caused by fungal, microbial and viral infections, vitilago, systemic lupus erythromatosus, psoriasis, carcinoma, melanoma, as well as other mammal skin cancers, skin damage resulting from exposure to ultraviolet (UV) radiation, chemicals, heat, wind and dry environments, wrinkles, saggy skin, lines and dark circles around the eyes, dermatitis and other allergy related conditions of the skin. COX/LOX mediated diseases and conditions of the mouth, teeth and gums, include, but not limited to periodontal diseases, oral pre-cancerous conditions, oral cancers, and other oral malignancies, sensitive gums and teeth, sequelae, pulpitis, irritation, pain and inflammation caused by the physical implantation of oral dentures, trauma, injuries, bruxism and other minor wounds in mouth, on the gums or on the tongue, dental plague and calculus, tooth decalcification, proteolysis and caries (decay).

The present invention further includes methods for the prevention and treatment of other COX and LOX mediated diseases and conditions, including but not limited to general joint pain and stiffness, lack of mobility and loss of physical function due to pathological conditions of osteoarthritis and rheumatoid arthritis, menstrual cramps, arteriosclerosis, obesity, diabetes, Alzheimer's disease, respiratory allergic reaction, chronic venous insufficiency, psoriasis, chronic tension headache, migraine headaches, inflammatory bowel disease, prostate cancer and other solid tumors.

The method for preventing and treating said COX and LOX mediated diseases and conditions is comprised of administering to a host in need thereof an effective amount of a composition comprising bakuchiol, which is substantially free of furanocumarin impurities together with a pharmaceutically acceptable carrier. As noted above, the amount of bakuchiol in the composition is in the range of 27% to 100%. In preferred embodiments the amount of bakuchiol in the composition is approximately 30%. Also as noted above, in preferred embodiments, the bakuchiol is isolated from a plant or plants in the *Psorlea* genus of plants.

Further included in the present invention are methods for the prevention and treatment of diseases and conditions of the skin, mouth, teeth or gums mediated by microbial infections, including but not limited to bacterial, viral and fungal infections, said method comprising administering to a host in need thereof an effective amount of a pharmaceutical composition comprised of bakuchiol, which is substantially free of furanocoumarin impurities together with a pharmaceutically acceptable carrier. Diseases and conditions of the skin, mouth, gums and teeth mediated by microbial infections include, but are not limited to dandruff, acne, athletes foot, periodontal diseases, selected from the group consisting of caries, gingivitis, periodontitis, pulpitis, periodontal conditions caused by the physical implantation of oral dentures, trauma, injuries, bruxism, neoplastic and other degenerative processes; material alba, pellicles, dental plagues, calculus and stains.

In one embodiment, the bacterium is selected from *Propionibacterium acnes* or *Staphylococcus epidermidis*.

The compositions of this invention can be administered by any method known to one of ordinary skill in the art. The modes of administration include, but are not limited to, enteral (oral) administration, parenteral (intravenous, subcutaneous, and intramuscular) administration and topical application. In preferred embodiments the compositions are administered topically. The method of prevention and treatment according to this invention comprises administering internally or topically to a patient in need thereof a therapeutically effective amount a composition comprised of bakuchiol, which is substantially free of impurities, particularly furanocoumarin impurities.

The method of prevention and treatment according to this invention comprises administering systemically or topically to a host in need thereof a therapeutically effective amount of UP256 (bakuchiol) synthesized and/or isolated from a single plant or multiple plants and a pharmaceutically acceptable carrier. The purity of the UP256 includes, but is not limited to 30% to 100%, depending on the methodology used to obtain and purify the compound. In a preferred embodiment, doses of UP256 an efficacious, nontoxic quantity generally selected from the range of 0.001% to 100% based on total weight of the topical formulation and/or 0.001-200 mg per kilogram based on the total body weight of the host. Persons skilled in the art using routine clinical testing are able to determine optimum doses for the particular ailment being treated.

The present invention includes an evaluation of different compositions of UP256 (bakuchiol) synthesized and/or isolated from a single plant or multiple plants and a pharmaceutically acceptable carrier using enzyme, receptor, microbial and other in vitro and in vivo models to optimize the formulation and obtain the desired physiological activity. The compositions of this invention can be administered by any method known to one of ordinary skill in the art. The modes of administration include, but are not limited to, enteral (oral) administration, parenteral (intravenous, subcutaneous, and intramuscular) administration and topical application. The method of treatment according to this invention comprises administering internally or topically to a patient in need thereof a therapeutically effective amount of UP256 (bakuchiol) synthesized and/or isolated from a single plant or multiple plants, wherein said bakuchiol is substantially free of furanocoumarin impurities. In a one embodiment the composition is administered topically. Methods for topical administration include, but are not limited to a toothpaste, gel, ointment, mouthwash, chewing gum, tinctures, drinks and as well as other known pharmaceutical formulations. When formulated in a toothpaste, the content of the composition can be in the range of 0.1 to 2 weight percent (%) of bakuchiol.

The compositions of the present invention can be formulated as pharmaceutical compositions, which include other components such as a pharmaceutically and/or cosmetically acceptable excipient, an adjuvant, and/or a carrier. For example, compositions of the present invention can be formulated in an excipient that the host to be treated can tolerate. An excipient is an inert substance used as a diluent or vehicle for a drug. Examples of such excipients include, but are not limited to water, buffers, saline, glycerin, hydrated silica, propylene glycol, aluminum oxide, carrageenan, cellulose gum, titanium dioxide, Ringer's solution, dextrose solution, mannitol, Hank's solution, preservatives and other aqueous physiologically balanced salt solutions. Nonaqueous vehicles, such as fixed oils, sesame oil, ethyl oleate, or triglycerides may also be used. Other useful formulations include suspensions containing viscosity enhancing agents, such as sodium carboxymethylcellulose, sorbitol, or dextran. Excipients can also contain minor amounts of additives, such as EDTA, disodium DDTA, BHA, BHT, diammonium citrate, nordihydroguaiaretic acid, propyl gallate, sodium gluconate, Sodium metabisulfite, t-butyl hydroquinone, $SnCl_2$, $H_2O_2$, and 2,4,5-trihydroxybutyrophenone, vitamin C vitamin E and other substances that enhance isotonicity and chemical stability. Examples of substances for adjusting pH of the formulation include sodium hydroxide, sodium carbonate, sodium bicarbonate, pentasodium triphosphate, tetrasodium pyrophosphate, sodium lauryl sulfate, calcium peroxide, phosphate buffer, bicarbonate buffer, tris buffer, histidine, citrate, and glycine, or mixtures thereof, while examples of flavors include, but are not limited to thimerosal, m- or o-cresol, formalin, fruit extracts and benzyl alcohol. Standard formulations can either be liquid or solids, which can be taken up in a suitable liquid as a suspension or solution for administration. Thus, in a non-liquid formulation, the excipient can comprise dextrose, human serum albumin, preservatives, etc., to which sterile water or saline can be added prior to administration.

In one embodiment of the present invention, the composition can also include an adjuvant or a carrier. Adjuvants are typically substances that generally enhance the biological response of a mammal to a specific bioactive agent. Suitable adjuvants include, but are not limited to, Freund's adjuvant;

other bacterial cell wall components; aluminum, calcium, copper, iron, zinc, magnesium, stannous based salts: silica; polynucleotides; toxoids; serum proteins; viral coat proteins; other bacterial-derived preparations; gamma interferon; block copolymer adjuvants, such as Hunter's Titermax adjuvant (Vaxcel™, Inc. Norcross, Ga.); Ribi adjuvants (available from Ribi ImmunoChem Research, Inc., Hamilton, Mont.); and saponins and their derivatives, such as Quil A (available from Superfos Biosector A/S. Denmark). Carriers are typically compounds that increase the half-life of a therapeutic composition in the treated host. Suitable carriers include, but are not limited to, polymeric controlled release formulations, biodegradable implants, liposomes, bacteria, viruses, oils, esters, and glycols.

In one embodiment, the composition is prepared as a controlled release formulation, which slowly releases the composition of the present invention into the host. As used herein, a controlled release formulation comprises a composition of the present invention in a controlled release vehicle. Suitable controlled release vehicles will be known to those skilled in the art. Preferred controlled release formulations are biodegradable (i.e., bioerodible).

The therapeutic agents of the instant invention are administered topically by any suitable means, known to those of skill in the art for topically administering therapeutic compositions including, but not limited to as an ointment, gel, lotion, or cream base or as an emulsion, as a patch, dressing or mask, a nonsticking gauze, a bandage, a swab or a cloth wipe. Such topical application can be locally administered to any affected area, using any standard means known for topical administration. A therapeutic composition can be administered in a variety of unit dosage forms depending upon the method of administration. For particular modes of delivery, a therapeutic composition of the present invention can be formulated in an excipient of the present invention. A therapeutic reagent of the present invention can be administered to any host, preferably to mammals, and more preferably to humans. The particular mode of administration will depend on the condition to be treated.

In one embodiment, a suitable ointment is comprised of the desired concentration of UP256 (bakuchiol) that is an efficacious, nontoxic quantity generally selected from the range of 0.001% to 100% based on total weight of the topical formulation, from 65% to 100% (preferably 75% to 96%) of white soft paraffin, from 0% to 15% of liquid paraffin, and from 0% to 7% (preferably 3 to 7%) of lanolin or a derivative of synthetic equivalent thereof. In another embodiment the ointment may comprise a polyethylene-liquid paraffin matrix.

In one embodiment, a suitable cream is comprised of an emulsifying system together with the desired concentration of UP256 (bakuchiol) synthesized and/or isolated from a single plant or multiple plants as provided above. The emulsifying system is preferably comprised of from 2 to 10% of polyoxyethylene alcohols (e.g. the mixture available under the trademark Cetomacrogol™ 1000), from 10 to 25% of stearyl alcohol, from 20 to 60% of liquid paraffin, and from 10 to 65% of water, together with one or more preservatives, for example from 0.1 to 1% of N,N"-methylenebis[N'-[3-(hydroxymethyl)-2,5-dioxo-4-imidazolidinyl]urea](available under the name Imidurea USNF), from 0.1 to 1% of alkyl 4-hydroxybenzoates (for example the mixture available from Nipa Laboratories under the trade mark Nipastat), from 0.01 to 0.1% of sodium butyl 4-hydroxybenzoate (available from Nipa Laboratories under the trade mark Nipabutyl sodium), and from 0.1 to 2% of phenoxyethanol.

In one embodiment, a suitable gel is comprised of a semi-solid system in which a liquid phase is constrained within a three dimensional polymeric matrix with a high degree of cross-linking. The liquid phase may be comprised of water, together with the desired amount of UP256 (bakuchiol), from 0 to 20% of water-miscible additives, for example glycerol, polyethylene glycol, or propylene glycol, and from 0.1 to 10%, preferably from 0.5 to 2%, of a thickening agent, which may be a natural product, for example tragacanth, pectin, carrageen, agar and alginic acid, or a synthetic or semi-synthetic compound, for example methylcellulose and carboxypolymethylene (carbopol); together with one or more preservatives, for example from 0.1 to 2% of methyl 4-hydroxybenzoate (methyl paraben) or phenoxyethanol-differential. Another suitable base, is comprised of the desired amount of UP256 (bakuchiol), together with from 70 to 90% of polyethylene glycol (for example, polyethylene glycol ointment containing 40% of polyethylene glycol 3350 and 60% of polyethylene glycol 400, prepared in accordance with the U.S. National Formulary (USNF)), from 5 to 20% of water, from 0.02 to 0.25% of an anti-oxidant (for example butylated hydroxytoluene), and from 0.005 to 0.1% of a chelating agent (for example ethylenediamine tetraacetic acid (EDTA)).

The term soft paraffin as used above encompasses the cream or ointment bases white soft paraffin and yellow soft paraffin. The term lanolin encompasses native wool fat and purified wool fat. Derivatives of lanolin include in particular lanolins which have been chemically modified in order to alter their physical or chemical properties and synthetic equivalents of lanolin include in particular synthetic or semisynthetic compounds and mixtures which are known and used in the pharmaceutical and cosmetic arts as alternatives to lanolin and may, for example, be referred to as lanolin substitutes.

One suitable synthetic equivalent of lanolin that may be used is the material available under the trademark Softisan™ known as Softisan 649. Softisan 649, available from Dynamit Nobel Aktiengesellschaft, is a glycerine ester of natural vegetable fatty acids, of isostearic acid and of adipic acid; its properties are discussed by H. Hermsdorf in Fette, Seifen, Anstrichmittel, Issue No. 84, No. 3 (1982), pp. 3-6.

The other substances mentioned hereinabove as constituents of suitable ointment or cream bases and their properties are discussed in standard reference works, for example pharmacopoeia. Cetomacrogol 1000 has the formula $CH_3(CH_2)m(OCH_2CH_2)_nOH$, wherein m may be 15 or 17 and n may be 20 to 24. Butylated hydroxytoluene is 2,6-di-tert-butyl-p-cresol. Nipastat is a mixture of methyl, ethyl, propyl and butyl 4-hydroxybenzoates.

The compositions of the invention may be produced by conventional pharmaceutical techniques. Thus the aforementioned compositions, for example, may conveniently be prepared by mixing together at an elevated temperature, preferably 60-70° C., the soft paraffin, liquid paraffin if present, and lanolin or derivative or synthetic equivalent thereof. The mixture may then be cooled to room temperature, and, after addition of the hydrated crystalline calcium salt of mupirocin, together with the corticosteroid and any other ingredients, stirred to ensure adequate dispersion.

Regardless of the manner of administration, the specific dose is calculated according to the approximate body weight of the host. Further refinement of the calculations necessary to determine the appropriate dosage for treatment involving each of the above mentioned formulations is routinely made by those of ordinary skill in the art and is within the scope of tasks routinely performed by them without undue experimentation, especially in light of the dosage information and assays disclosed herein. These dosages may be ascertained through use of the established assays for determining dosages utilized in conjunction with appropriate dose-response data.

It should be noted that the invention described herein may be used for veterinary as well as human applications and that the term "host" should not be construed in a limiting manner. In the case of veterinary applications, the dosage ranges can be determined as described above, taking into account the body weight of the animal.

EXAMPLES

The following examples are provided for illustrative purposes only and are not intended to limit the scope of the invention.

Example 1. Method for the Quantification of Bakuchiol, Psoralen and Isopsoralen by HPLC The amount of bakuchiol, psoralen and isopsoralen in the extracts, fractions, and the novel composition generated as described below was quantified by a high pressure liquid chromatography (HPLC) using a PhotoDiode Array detector (HPLC/PDA) and a Luna Phenyl-hexyl column (250 mm×4.6 mm). The targeted compounds were eluted from the column using an acetonitrile (ACN) water gradient from 36% to 100% ACN over a period of 12 minutes, followed by 100% ACN for three minutes. The detailed HPLC conditions used are set forth in Table 1. A chromatogram of the HPLC separation is depicted in FIG. 1. The targeted compounds were identified and quantified based on retention time and UV peak area using commercially available pure bakuchiol, psoralen and isopsoralen as quantification standards. The retention times for the bakuchiol, psoralen and isopsoralen were 18.19 minutes, 7.33 minutes and 7.95 minutes, respectively.

TABLE 1

HPLC Conditions for quantification of Bakuchiol, Psoralen and Isopsoralen

| Column | Luna Phenyl-hexyl, 150 × 4.6 mm |
|---|---|
| Gradient | 0-8 min 36% ACN/water |
| | 8-20 min 36% ACN/water to 100% ACN |
| | 20-23 min 100% ACN |
| | 23-28 min 36% ACN/water |

TABLE 1-continued

HPLC Conditions for quantification of Bakuchiol, Psoralen and Isopsoralen

| Column | Luna Phenyl-hexyl, 150 × 4.6 mm |
|---|---|
| Flow rate | 1 mL/min |
| Detection | 0-11 min 246 nm (for psoralen and angelicin, 7-8 min) |
| | 11-28 min 260 nm (for bakuchiol, 18-19 min) |
| Temperature | 35° C. |
| Standard concentration | 0.1 mg/mL in MeOH for bakuchiol |
| | 0.025 mg/mL for psoralen and angelicin |
| Extract preparation | 0.2 mg/mL in MeOH |
| Linear range | 0.01 mg/mL to 0.15 mg/mL |

Example 2. General Methods for the Extraction of Bakuchiol from *Psoralea* Plants Wrist Shaker To a flask was added solvent (100 mL) and *Psoralea corylifolia* seed powder (10 g) and the mixture was shaken on a wrist shaker at room temperature for one hour. The mixture was then passed through a filter and the filtrate collected. The extraction process was repeated one more time with fresh solvent, the filtrates were combined, the solvent removed on a rotoevaporator and the residue was dried under high vacuum.

Reflux

To a flask was added solvent (50 mL) and *Psoralea corylifolia* seed powder (10 g) and the mixture was refluxed for 40 min. The solution was then filtered and the extraction process was repeated two more times with fresh solvent. The filtrates were combined and the solvent was evaporated to obtain a dried extract.

Following above extraction methods, sample plant material was extracted with the following solvents: dichloromethane (DCM). EtOAc, acetone, MeOH, petroleum ether (BP 35-60° C.) and petroleum ether (BP 60-90° C.). The extracts were then analyzed by HPLC analysis as described in Example 1. The results are set forth in Table 2.

TABLE 2

Quantification of various *Psoralea corylifolia* extracts

| | Petroleum Ether (35-60° C.) | DCM | EtOAc | Acetone | MeOH | Petroleum Ether (35-60° C.) | Petroleum Ether (60-90° C.) |
|---|---|---|---|---|---|---|---|
| Extract wt. (g) | 0.5833 | 1.7535 | 1.6710 | 1.8932 | 1.8795 | 0.6457 | 0.9203 |
| % Bakuchiol in Extract | 29.1% | 14.2% | 13.7% | 13.7% | 13.9% | 25.6% | 27.2% |
| % Bakuchiol in Plant | 1.7% | 2.5% | 2.3% | 2.6% | 2.6% | 2.6% | 2.7% |
| Method | Wrist shaker (100 ml/10 g solid) | | | | | Reflux (50 ml/10 g solid) | |

Example 3. Large Scale Extraction of Bakuchiol from *Psoralea* Plants

Seed powder of *Psoralea corylifolia* (2 kg) and 9 liter of petroleum (pet.) ether (BP 60-90° C.) were rotated in a 20 L flask on a rotoevaporator at 70° C. in a water bath for 1 hour. The solution was then decanted into a separate container and the solvent was removed under vacuum. Fresh solvent was added into the biomass and the extraction process was repeated three more times. The extracts were combined and evaporated to yield 335 g of a crude extract (MH-258-01-01) having 21% bakuchiol and 3% psoralen/isopsoralen by weight.

Example 4. Evaluation of Various Chromatographic Methods for Purifying Bakuchiol Extracts Various chromatographic methods for purifying the crude solvent extract (MH-206-70-1) isolated from the seeds of *Psoralea corylifolia* using the method described in Example 2, were evaluated to determine the potential for using column chromatography as a means of obtaining high purity bakuchiol free of contamination by furanocoumarins, particularly psoralen/isopsoralen contamination. Briefly, each empty column cartridge (1.3 cm ID and 20 mL capacity, from Bio-Rad) was packed with a different and eluted with different solvents in an attempt to separate the furanocoumarin impurities from bakuchiol. The fractions (10 mL per fraction) were collected in test tubes and analyzed with silica gel TLC plates developing with 20% EtOAc/petroleum ether. The targeted compounds, bakuchiol, psoralen and isopsoralen were identified based on their retention times, which were determined using standard solutions. The results are set forth in Table 3.

TABLE 3

Summary of column chromatographic separation of bakuchiol from furanocoumarins in crude extracts of *Psoralea corylifolia*

| Media | Column size/ Extract Loading | Elution Solvent | Results |
|---|---|---|---|
| Al₂O₃ (neutral) (J.T. Baker) | 2 mL/25 mg | 1. petroleum ether<br>2. EtOAc<br>3. MeOH | Little separation |
| XAD-4 (amerlite polystyrene resin) | 5 mL/19 mg | MeOH/water gradient in 20% increments from 100% water to 100% MeOH | No separation |
| XAD-7 (amerlite polyacrylate resin) | 8 mL/16 mg | pet. ether/EtOAc gradient in 20% increments from 100% petroleum ether to 100% MeOH | Some separation |
| | | MeOH/water gradient in 20% increments from 100% water to 100% MeOH | Little separation |
| Polyamide | 5 mL/50 mg | 1. petroleum ether<br>2. 5% acetone/pet. ether<br>3. acetone | No separation |
| LH-20 | 8 mL/50 mg | petroleum ether | No separation |
| Silica gel | 5 mL/50 mg | 1. petroleum ether<br>2. 15% EtOAc/pet. ether | Good separation |
| CG-71md | 5 mL/50 mg | 1. petroleum ether<br>2. acetone | No separation |
| CG-161cd | 5 mL/50 mg | petroleum ether | No separation |
| | 6 mL/50 mg | MeOH/water step gradient | Good separation<br>Low yield |

Example 5. Hydrolysis of a Petroleum Ether Extract Isolated from the Seeds of *Psoralea corylifolia*

A petroleum ether extract (25 g; MH-258-01-01), isolated from the seeds of *Psoralea corylifolia* as described in Example 3, was mixed with 500 mL of a NaOH solution (56.5 mM) in a 1 L round bottom flask. The solution was refluxed in a heating mantel for one hour. A small portion of the solution was taken from the flask periodically and analyzed by HPLC as described in Example 1. The reaction was stopped after HPLC analysis showed that the peaks for psoralen and isopsoralen had completely disappeared. The reaction mixture was then cooled to room temperature to yield a dark brown solution having a solid content of approximately 36 mg/mL (MH-258-10-01).

Figure 3:
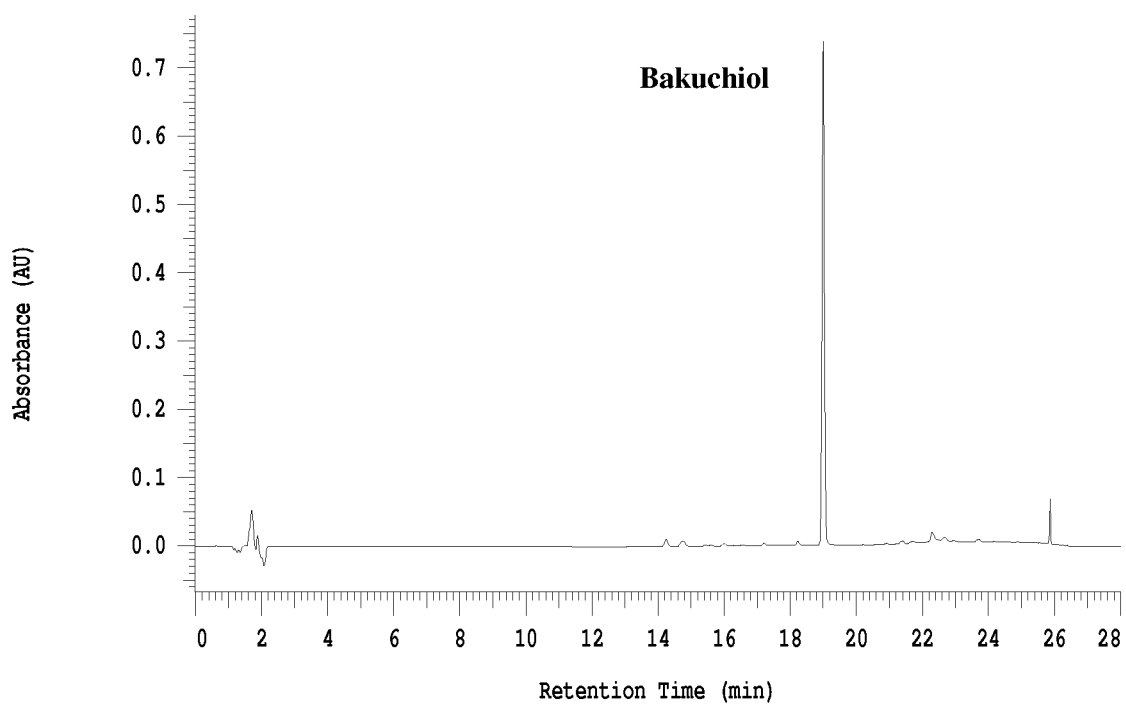
FIG. 3 depicts the HPLC chromatogram of a UP256 sample (MH-258-07-01) comprised of 31% bakuchiol.

To 20 mL of the hydrolysis solution (MH-258-10-01) in a separatory funnel (150 mL) was added DCM (20 mL). The mixture was shaken for 10 min and the layers were allowed to separate. The DCM layer was removed from the bottom of the separatory funnel and the extraction was repeated one more time with 20 mL of fresh DCM. The organic layers were combined, and the solvent removed by rotary evaporation under vacuum to yield 118 mg of a composition (MH-258-07-01), which contained 31% bakuchiol and was free of furanocoumarin contaminants (FIG. 3).

Figure 4:
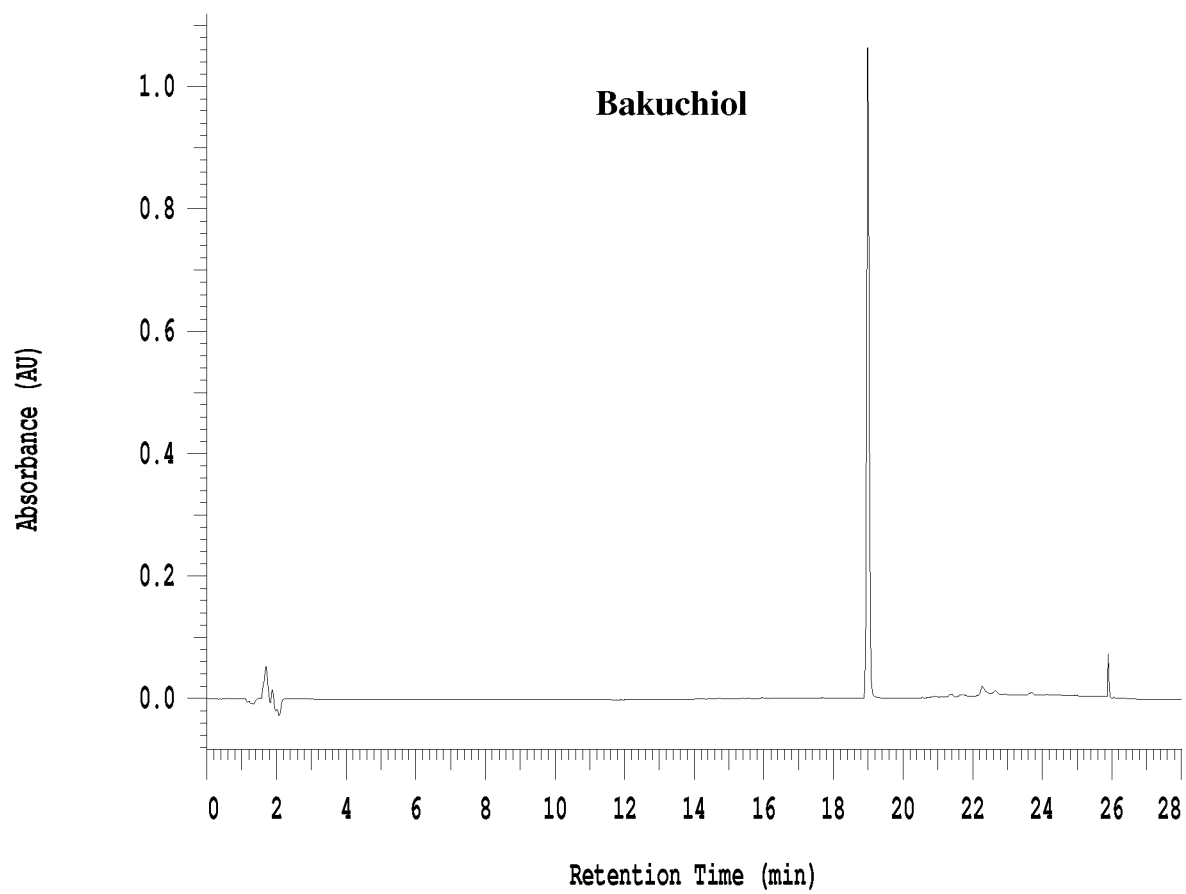
FIG. 4 depicts the HPLC chromatogram of a UP256 sample (MH-258-07-02) comprised of 41% bakuchiol.

To 20 mL of the hydrolysis solution (MH-258-10-01) in a separatory funnel (150 mL) was added petroleum ether (20 mL). The mixture was shaken for 10 min. and the layers were allowed to separate. The petroleum ether layer was removed from the top of the separatory funnel and the extraction was repeated one more time with 20 mL of fresh petroleum ether. The organic layers were combined and the solvent removed by rotary evaporation under vacuum to yield 136 mg of a composition (MH-258-07-02), which contained 41% bakuchiol and was free of furanocoumarin contaminants (FIG. 4).

Example 6. Hydrolysis of a Methanol Extract Isolated from the Seeds of *Psoralea corylifolia*

A dried methanol extract (MH-293-68-01), isolated from the seeds of *Psoralea corylifolia* as described in Example 2, was mixed with 1 L of a NaOH solution (44 g NaOH in DI water) in a 2 L beaker on a stirrer/hot plate. The solution was stirred while boiling for 2 hours. Water was added to the beaker as necessary to maintain the total volume at about 1200 mL. After 2 hours the solution was allowed to cool to room temperature, after which time 600 mL was transferred to a separatory funnel. Petroleum ether (250 mL) was added and the mixture was shaken for 10 min. and the layers were allowed to separate. The petroleum ether layer was removed from the top of the separatory funnel and the extraction was repeated (3×) with fresh solvent. The organic extracts were combined and the solvent removed by rotary evaporation under vacuum to yield 2.25 g of a composition (MH-293-74-01), which contained 51% bakuchiol and was free of furanocoumarin contaminants.

Example 7. Hydrolysis of Petroleum Ether Extract Isolated from the Seeds of *Psoralea corylifolia* Followed by Purification by Column Chromatography A petroleum ether extract (25 g; MH-258-01-01), isolated from the seeds of *Psoralea corylifolia* as described in Example 3, was mixed with 500 mL of a NaOH solution (56.5 mM) in a 1 L round bottom flask. The solution was refluxed for one hour. A small portion of the solution was taken from the flask periodically and analyzed by HPLC as described in Example 1. The reaction was allowed to proceed until HPLC analysis showed that the peaks for psoralen and isopsoralen had completely disappeared. The reaction mixture was then cooled to room temperature to yield a dark brown solution having a solid content of approximately 36 mg/mL (MH-258-10-01).

Figure 5:
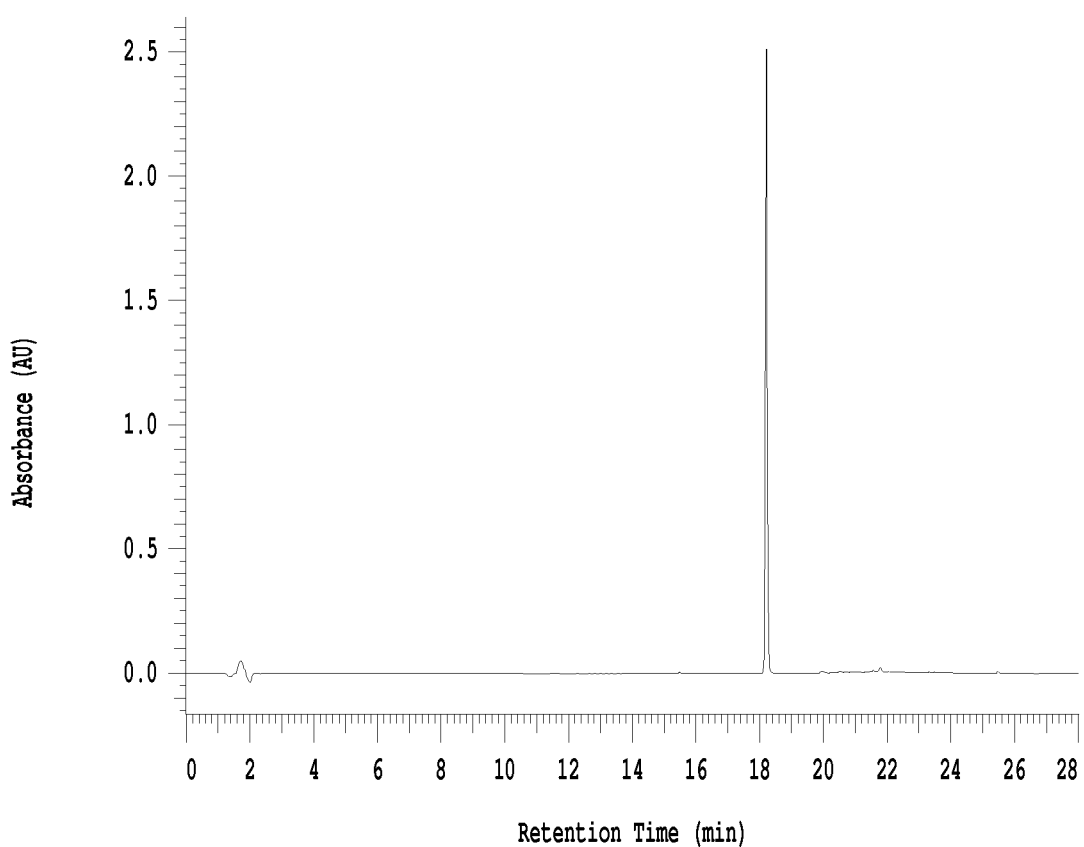
FIG. 5 depicts the HPLC chromatogram of a UP256 sample (MH-258-12-08) comprised of 99% bakuchiol.

150 mL of this solution (MH-258-10-01) was loaded onto a pre-prepared CG-161cd column. The pre-prepared column (5×13 cm) contained 300 mL of CG-161cd resin, which had been equilibrated with 4 column volumes of DI water. The loading material (MH-258-10-01) was fed into the top of the column and eluted with 2500 mL of DI water to bring the column to pH 7, followed by 2500 mL of 70% MeOH/water and 4500 mL of 90% MeOH/water to elute bakuchiol. The eluent was monitored by TLC until the bakuchiol was completely eluted from the column. Fractions containing only bakuchiol (2 L) were combined and evaporated under vacuum to remove the solvent. Using this method highly pure bakuchiol (2.3 g) (99% pure, MH-258-12-08 and -09), free of furanocoumarin contamination was obtained. (See FIG. 5). Earlier and later bakuchiol fractions were also collected, combined and evaporated under vacuum. From these fractions a composition (MH-258-12-07 and -10) was obtained in a quantity of 2.4 grams, which contained 70% bakuchiol free of furanocoumarin contamination. The loading capacity of the CG-161cd column was estimated as 400 mL of the crude hydrolysis solution per liter of CG-161cd resin. After separation, the CG-161cd column was recovered by washing with Clorox followed with MeOH and 4 column volumes of DI water. It can be reused for a number of years.

Example 8. Inhibition of COX-1 and COX-2 by Purified Bakuchiol

In order to screen for compounds that inhibited COX-1 and COX-2 activity, a high throughput, in vitro assay was developed that utilized the inhibition of the peroxidase activity of both enzymes. (Needleman et al. (1986) Annu Rev Biochem. 55:69). Briefly, the composition or compound being examined was titrated against a fixed amount of COX-1 and COX-2 enzymes. A cleavable, peroxide chromophore was included in the assay to visualize the peroxidase activity of each enzyme in presence of arachidonic acid as a cofactor. Typically, assays were performed in a 96-well format. Each inhibitor, taken from a 10 mg/mL stock solution in 100% DMSO, was tested in triplicate at room temperature using the following range of concentrations: 0, 0.1, 1, 5, 10, 20, 50, 100, and 500 µg/mL. To each well, 150 µL of 100 mM Tris-HCl, pH 7.5 was added along with 10 µL of 22 µM Hematin diluted in tris buffer, 10 µL of inhibitor diluted in DMSO and 25 units of either the COX-1 or COX-2 enzyme. The components were mixed for 10 seconds on a rotating platform, followed by the addition of 20 µL of 2 mM N,N,N'N'-tetramethyl-p-phenylenediamine dihydrochloride (TMPD) and 20 µL of 1.1 mM arachidonic acid to initiate the reaction. The plate was shaken for 10 seconds and then incubated 5 minutes before reading the absorbance at 570 nm. The inhibitor concentration vs. % inhibition was plotted and the $IC_{50}$ determined by taking the half-maximal point along the isotherm and intersecting the concentration on the X-axis. The $IC_{50}$ was then normalized to the number of enzyme units in the assay. A high purity (99%) bakuchiol sample (MH-258-08 was tested for both COX-1 and COX-2 inhibition. The results are summarized in the following Table 4.

TABLE 4

Inhibition of COX activity by bakuchiol

| Compound Name | COX-1 ($IC_{50}$) | COX-2 ($IC_{50}$) |
|---|---|---|
| MH-258-08 (99% bakuchiol) | 2.34 µM | 5.78 µM |

Example 9. Inhibition of 5-Lipoxygenase by Purified Bakuchiol (MH-258-12-08)

As noted above, one of the most important pathways involved in the inflammatory response is produced by non-heme, iron-containing lipoxygenases (5-LOX, 12-LOX, and 15-LOX), which catalyze the oxidation of fatty acids such as AA to produce the hydroperoxides 5-, 12- and 15-HPETE, which are then converted to leukotrienes. A Lipoxygenase Inhibition Assay was carried out using a published method (Carter et al. (1991) J. Pharmacol. Exp. Ther. 256(3):929-937, Safayhi et al. (2000) Planta Medica. 66:110-113). 5-LOX was isolated from human PBML cells and arachidonic acid was utilized as a substrate. The test article and positive control were dissolved in 1% DMSO. HBSS (Hank's balanced salt solution) was used as incubation buffer. Pre-incubation time was 15 minutes at 37° C., followed by 15 min. incubation at the same temperature. This assay detects the formation of LTB4 with EIA quantification. Highly pure bakuchiol (99% bakuchiol, #MH-258-12-08) was tested in duplicate at concentrations of 10 µM, 1 µM, 0.1 µM, and 10 nM relative to a positive control-NDGA at five concentrations. The dose response curve is illustrated in the FIG. 6. The $IC_{50}$ for 5-LOX inhibition by bakuchiol (99% pure) was 3.41 µM.

Example 10. Antimicrobial Activity of Purified Bakuchiol

The anti-microbial activity of a highly pure bakuchiol sample (99% pure; #MH-258-12-08) was evaluated using published methods (Modugno et al. (1994) Antimicrobial Agents & Chemotherapy 38:2362-2368; Misiek et al. (1973) Antimicrobial Agents & Chemotherapy 3:40-48). Briefly, *Staphylococcus epidermidis* (Gram Positive. ATCC 12228) was cultured for 20 hours at 37° C. in Mueller-Hinton Broth medium. *Propionibacterium acnes* (ATCC 6919) was cultured for 2 days at 37° C. in Reinforced Clostridial medium. The test article and positive control were dissolved in 1% DMSO with an incubation volume of 1 mL. The time of assessment was 1 day. Measurement of turbidity was used as the method of quantification. A highly pure bakuchiol sample (99%; #MH-258-12-08) was tested in duplicate at concentrations of 100 µg/mL, 30 µg/mL, 10 µg/mL, 3 µg/mL, 1 µg/mL, 0.3 µg/mL, 0.1 µg/mL and 0.03 µg/mL relative to positive controls-gentamicin at 0.1 µg/mL for *Staphylococcus epidermidis* and ampicillin at 0.1 µg/mL for *Propionibacterium acnes*, respectively. Significant inhibition was exhibited by bakuchiol at 1 µg/ml against both *Staphylococcus epidermidis* and *Propionibacterium acnes*. The highly pure sample of bakuchiol also inhibited the activity of *Trichophyton mentagrophytes* (ATCC 9533) at a moderate concentration of 30 µg/mL. Finally, no inhibition was observed for *Epidermophyton floccosum* (ATCC 18397), *Microsporum canis* (ATCC 36299) and *Pityrosporum ovale* (ATCC 38593).

Example 11. Evaluation of Acute Toxicity of Purified Bakuchiol

Acute Toxicity studies were completed testing two purity levels of bakuchiol (UP256) (a sample that was approximately 20% pure and a sample which was 99% pure). Forty female ICR mice (Harlan) aged 4-5 weeks old were used for the 14-day study. Mice were administered 100 mL of the acute dose daily, approximately 2 g/kg by weight per test article per day. The first 10 mice received the composition containing 20.7% bakuchiol, while the second group of 10 mice received a composition containing 99% bakuchiol. The UP256 composition was suspended in water and administered through a syringe. Twenty mice were administered water, as the control group. The weights of all mice were measured, including baseline, 3 mid points, and an endpoint. Also, food and water consumption were observed for all groups. Any abnormal health conditions or behavior was recorded over the two-week period. A necropsy of all mice was completed on day 14 and blood from all groups was collected for a complete blood screen. Two mice picked randomly from each of groups also had kidney and liver tissues removed for Histopathology. All blood work and pathology work was completed through Antech Diagnostics.

The average weight calculated for all groups, including controls, continued to increase over the two-week study period. No mouse showed a decrease in weight, and food/water consumption remained the same for all groups. Aggression towards the investigator (i.e. biting) and towards each other (i.e. fighting in cage) was the only significant difference in behavior among the treated mice compared to the control mice. This is a behavior that would be expected in the mice receiving androgen, a male hormone. The necropsy of all mice showed no gross abnormalities or changes in any organ. The blood work showed the treated groups were normal relative to the controls. The protein, enzyme, and ion levels were within normal values for ICR mice. The kidney and liver tissues were sent for Histopathology to assess any micro changes in the organs and the report stated that significant changes were not present in the kidney and the hepatocyte nuclei for the liver were within normal limits for mice. There was no substantial inflammation or evidence of neoplasia in either tissue section examined.

In conclusion, all weights, blood work, and histological data, was the same for the treated mice relative to the control group. No adverse effects were observed in the fourteen-day study for either sample of UP256. Therefore, it can be concluded that UP256 at both purity levels (20% and 99% purity) has a solid safety profile.

What is claimed is:

1. A method for preventing or treating cyclooxygenase (COX) and lipoxygenase (LOX) mediated diseases or conditions of the skin, teeth, mouth or gums, the method comprising administering to a host in need thereof an effective amount of a pharmaceutical composition comprising bakuchiol and substantially no furanocoumarin impurities, wherein the amount of bakuchiol in the composition ranges from about 27% to 100% by weight.

2. The method of claim 1, wherein the COX and LOX mediated diseases and conditions of the skin are: sun burn; thermal burns; acne; dandruff; topical wounds; minor inflammatory conditions caused by fungal, microbial or viral infection; vitiligo; systemic lupus; erthyematosus; psoriasis; carcinoma; melanoma; skin damage resulting from exposure to ultraviolet (UV) radiation, chemicals, heat, wind or dry environments; wrinkles; saggy skin; lines or dark circles around the eyes; or dermatitis.

3. The method of claim 1, wherein the COX and LOX mediated diseases and conditions of the teeth, mouth, or gums are: periodontal diseases; oral pre-cancerous conditions; oral cancers; sensitive gums or teeth; sequelae; pulpitis; irritation; pain or inflammation caused by the physical implantation of oral dentures, trauma, injuries, bruxism, wounds in the mouth, on the gums, or on the tongue; dental plague or calculus; tooth decalcification; or proteolysis or caries.

4. The method of claim 1, wherein the administering the pharmaceutical composition to the host is by a route of administration selected from the group consisting of topical, aerosol, suppository, intradermic, intramuscular, and intravenous administration.

5. The method of claim 4, wherein the route of administration is topical.

6. The method of claim 5, wherein the pharmaceutical composition is administered using a nonsticking gauze, a bandage, a swab, a cloth wipe, a patch, a mask, a cleanser, an antiseptic, a solution, a cream, a lotion, an ointment, a gel, or an emulsion, a liquid, a paste, a soap, or a powder.

7. The method of claim 1, wherein the pharmaceutical composition further comprises an excipient that is pharmaceutically, dermatologically or cosmetically suitable for topical application, and optionally comprises an adjuvant, a carrier, controlled releasing vehicle or combinations thereof.

8. A method for the prevention or treatment of cyclooxygenase (COX) and lipoxygenase (LOX) mediated diseases or conditions, wherein the diseases and conditions are: general joint pain or stiffness; lack of mobility or loss of physical function due to osteoarthritis or rheumatoid arthritis; menstrual cramps; arteriosclerosis; obesity; diabetes; Alzheimer's disease; respiratory allergic reaction; chronic venous insufficiency; psoriasis; chronic tension headache; migraine headaches; inflammatory bowel disease; or solid tumors, the method comprising administering to a host in need thereof an effective amount of a pharmaceutical composition comprising bakuchiol and substantially no furanocoumarin impurities, wherein the amount of bakuchiol in the composition ranges from about 27% to 100% by weight.

9. A method for preventing or treating diseases or conditions of the skin, teeth, mouth or gums mediated by microbial infections, the method comprising administering to a host in need thereof an effective amount of a pharmaceutical composition comprising bakuchiol and substantially no furanocoumarin impurities, wherein the amount of bakuchiol in the composition ranges from 27% to 100% by weight.

10. The method of claim 9, wherein the microbial infection is a bacterial infection, a viral infection or a fungal infection.

11. The method of claim 10, wherein the bacteria is *Propionibacterium acnes* or *Staphylococcus epidermidis*.

12. The method of claim 9, wherein the diseases or conditions of the skin, teeth, mouth or gums are: dandruff; acne; athletes foot, topical wounds; periodontal disease; periodontal conditions caused by the physical implantation of oral dentures, trauma, injuries, bruxism, neoplastic or degenerative processes; material alba; pellicles; dental plagues; or calculus or stains.

13. The method of claim 9, wherein the administering the pharmaceutical composition to the host is by a route of administration selected from the group consisting of topical, aerosol, suppository, intradermic, intramuscular, and intravenous administration.

14. The method of claim 13, wherein the route of administration is topical.

15. The method of claim 14, wherein the composition is administered using a nonsticking gauze, a bandage, a swab, a cloth wipe, a patch, a mask, a cleanser, an antiseptic, a solution, a cream, a lotion, an ointment, a gel, an emulsion, a liquid, a paste, a soap, or a powder.

16. The method of claim 9, wherein the pharmaceutical composition further comprises an excipient that is pharmaceutically, dermatologically or cosmetically suitable for topical application and optionally comprises an adjuvant, a carrier, controlled releasing vehicle or combinations thereof.

17. The method of claim 1, wherein the cyclooxygenase (COX) and lipoxygenase (LOX) mediated disease or conditions are a mammalian skin cancer or an allergy related condition of the skin.

18. The method of claim 1, wherein the cyclooxygenase (COX) and lipoxygenase (LOX) mediated disease or condition is an oral malignancy.

19. The method of claim 8, wherein the cyclooxygenase (COX) and lipoxygenase (LOX) mediated disease or condition is prostate cancer.

20. The method of claim 9, wherein the condition of the skin, teeth, mouth or gums is caries, gingivitis, periodontitis or pulpitis.

* * * * *